(12) United States Patent
Maruyama et al.

(10) Patent No.: US 8,257,933 B2
(45) Date of Patent: Sep. 4, 2012

(54) DETECTION OF INFLAMMATORY DISEASE AND COMPOSITION FOR PREVENTION OR TREATMENT OF INFLAMMATORY DISEASE

(75) Inventors: Kenta Maruyama, Tokyo (JP); Koichi Matsuo, Tokyo (JP); Hisataka Yasuda, Shiga (JP)

(73) Assignees: Keio University, Tokyo (JP); Oriental Yeast Co., Ltd., Tokyo (JP)

( * ) Notice: Subject to any disclaimer, the term of this patent is extended or adjusted under 35 U.S.C. 154(b) by 425 days.

(21) Appl. No.: 12/227,244

(22) PCT Filed: May 12, 2006

(86) PCT No.: PCT/JP2006/309602
§ 371 (c)(1),
(2), (4) Date: Nov. 12, 2008

(87) PCT Pub. No.: WO2007/132512
PCT Pub. Date: Nov. 22, 2007

(65) Prior Publication Data
US 2009/0202469 A1 Aug. 13, 2009

(51) Int. Cl.
*G01N 33/53* (2006.01)
*G01N 33/49* (2006.01)
*C07K 14/51* (2006.01)
*C07K 14/705* (2006.01)

(52) U.S. Cl. .................... 435/7.1; 435/7.92; 530/350

(58) Field of Classification Search .................. None
See application file for complete search history.

(56) References Cited

U.S. PATENT DOCUMENTS
2003/0211106 A1* 11/2003 Tornetta et al. ............ 424/146.1

FOREIGN PATENT DOCUMENTS
WO    WO 02/092016     11/2002
WO    WO 2004/082635    9/2004

OTHER PUBLICATIONS

Grimaud et al. Receptor activator of nuclear factor kB ligand (RANKL)/Osteoprotegerin (OPG) ratio is increased in severe osteolytis. American Journal of Pathology vol. 163/No. 5 pp. 2021-2031 (Nov. 2003).*
Semmler et al. Methionine metabolism in an animal model of sepsis. Clin. Cem. Lab. Med. 46(10):1398-1402 (2008).*
Nociti et al. Cementoblast gene expression is regulated by *Porphyromonas gingivalis* lipopolysccharide partically vial Toll-like receptor-4/MD-2. Journal of Dent. Researc 83(8):602-607 (2004).*
Nagasawa et al. LPS-stimulated human gingival fibroblast inhibit the differentiation of monocytes into osteoclast through the productio of osteoproteerin. Clin. Exp. Immunol. 130:338-344 (2002).*
Sakurai et al. *Streptococcus pyogenes* infection induces septic arthritis with increased production of the receptor activator of the NF-kB ligand. Infection and Immunity, vol. 71/10:6019-6026 (Oct. 2003).*
El-Atrouni et al. HIV-associated opportunistic infections; bacterial infections. Special issue:Human immunodeficiency virus disease. Abstract. Lebanese Medical Journal, vol. 54/2:80-83 (2006).*
Suda, et al., "Suppression of Osteoprotegerin Expression by Prostaglandin $E_2$ is Crucially involved in Lipopolysaccharide-Induced Osteoclast Formation", The Journal of Immunology, vol. 172, No. 4, Feb. 15, 2004, pp. 2504-2510.
Moschen, et al., "The RANKL/OPG system is activated in inflammatory bowel disease and relates to the state of bone loss", Gut, vol. 54, No. 4, Apr. 2005, pp. 479-487.
Yasuda, Hisataka, "Signal transduction in osteoclast differentiation", Journal of Clinical Experimental Medicine, vol. 205, No. 3, Apr. 19, 2003, pp. 187-189 along with its English translation.
Maruyama, et al., "RANKL can induce tolerance against bacterial components", Proceedings of the Japanese Society for Immunology (JSI), vol. 35, 2005, pp. 184, (2-E-W26-13-O/P).
Gori, et al., "The Expression of Osteoprotegerin and RANK Ligand and the Support of Osteoclast Formation by Stromal-Osteoblast Lineage Cells Is Developmentally Regulated", Endocrinology, vol. 141, No. 12, Dec. 2000, pp. 4768-4776.
Gravallese, E. M., Bone destruction in arthritis, Ann Rheum Dis, vol. 61 (Suppl II), Nov. 2002, pp. ii84-ii86.
Hiroyama, et al., "Osteoclast formation and activity in the pathogenesis of osteoporosis in rheumatoid arthritis", Rheumatology, vol. 41, No. 11, Nov. 2002, pp. 1232-1239.
Rivollier, et al., "Immature dendritic cell transdifferentiation into osteolasts: a novel pathway sustained by the rheumatoid arthritis microenvironment", Blood, vol. 104, No. 13, Dec. 2004, pp. 4029-4037.
Anandarajah, et al., "Anti-RANKL Therapy for Inflammatory Bone Disorders: Mechanisms and Potential Clinical Applications", Journal of Cellular Biochemistry, vol. 97, No. 2, Feb. 2006, pp. 226-232.
Maruyama, et al., "Receptor activator of NF-kappa B ligand and osteoprotegerin regulate proinflammatory cytokine production in mice", Journal of Immunology, vol. 177, No. 6, Sep. 15, 2006, pp. 3799-3805. Stolina, et al., "RANKL is a marker and mediator of local and systemic bone loss in two rat models of inflammatory arthritis", Journal of Bone and Mineral Research, vol. 20, No. 10, Jun. 6, 2005, pp. 1756-1765.
Ziolkowska, et al., "High levels of osteoprotegerin and soluble receptor activator of nuclear factor kappa B ligand in serum of rheumatoid arthritis patients and their normalization after anti-tumor necrosis factor alpha treatment", Arthritis and Rheumatism, vol. 46, No. 7, Jul. 2002, pp. 1744-1753.
Skoumal, et al., "Osteoprotegerin and the receptor activator of NF-kappa B ligand in the serum and synovial fluid. A comparison of patients with longstanding rheumatoid arthritis and osteoarthritis", Rheumatology International, vol. 26, No. 1, May 12, 2005, pp. 63-69.

* cited by examiner

*Primary Examiner* — Elizabeth C Kemmerer
*Assistant Examiner* — Regina M Deberry
(74) *Attorney, Agent, or Firm* — Hamre, Schumann Mueller & Larson, P.C.

(57) ABSTRACT

A novel method for detection of an inflammatory disease and a novel composition for prevention or treatment of an inflammatory disease are provided. The method for detection of an inflammatory disease comprises using RANKL and/or OPG as a marker in a biological sample. The composition for prevention or treatment of an inflammatory disease comprises RANKL and/or M-CSF as an active ingredient.

4 Claims, 24 Drawing Sheets

Fig. 9
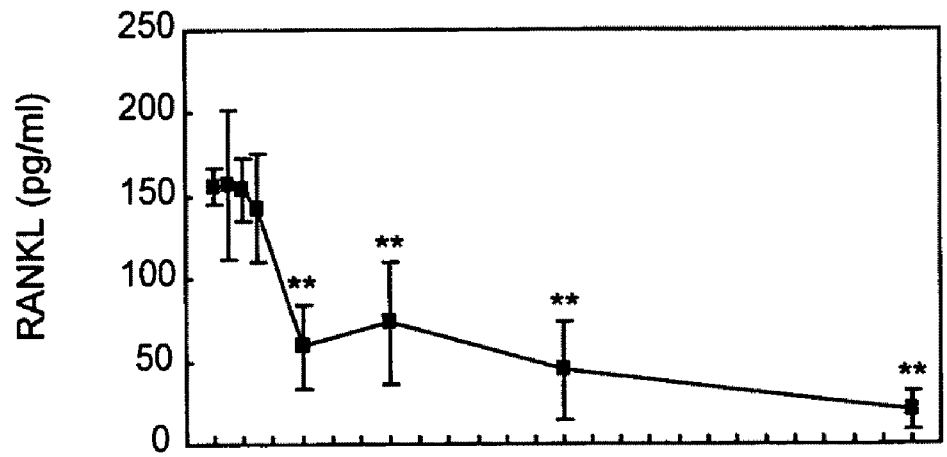
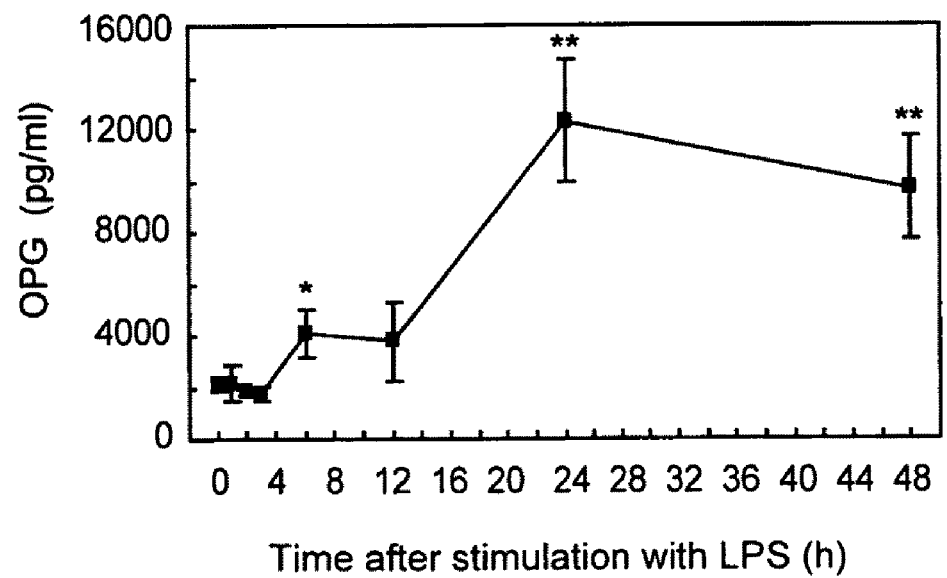

Fig. 10
A
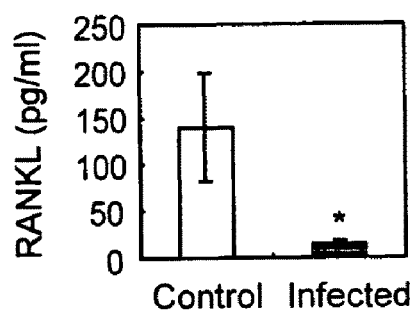
B
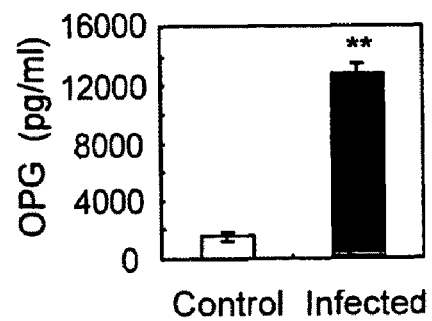

Fig. 11
A
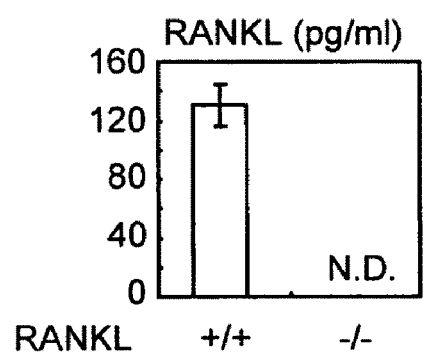
B
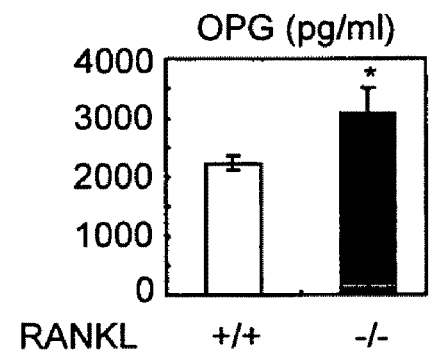

Fig. 13
A
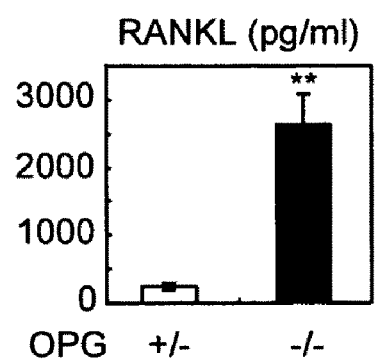
B
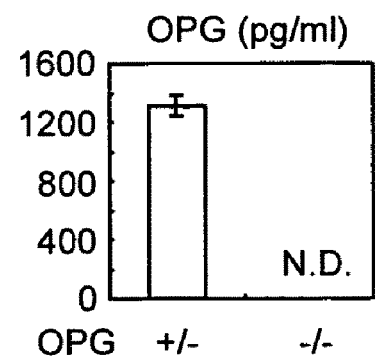

Fig. 19

```
         10        20        30        40        50        60
gtcgactATCAGAGCAGAGAAAGCGATGGTGGATGGCTCATGGTTAGATCTGGCCAAGAGGAGCAAG
 SalI   I R A E K A M V D G S W L D L A K R S K 70        80        90       100       110       120
CTTGAAGCTCAGCCTTTTGCTCATCTCACTATTAATGCCACCGACATCCCATCTGGTTCC
 L E A Q P F A H L T I N A T D I P S G S 130       140       150       160       170       180
CATAAAGTGAGTCTGTCCTCTTGGTACCATGATCGGGGTTGGGCCAAGATCTCCAACATG
 H K V S L S S W Y H D R G W A K I S N M 190       200       210       220       230       240
ACTTTTAGCAATGGAAAACTAATAGTTAATCAGGATGGCTTTTATTACCTGTATGCCAAC
 T F S N G K L I V N Q D G F Y Y L Y A N 250       260       270       280       290       300
ATTTGCTTTCGACATCATGAAACTTCAGGAGACCTAGCTACAGAGTATCTTCAACTAATG
 I C F R H H E T S G D L A T E Y L Q L M 310       320       330       340       350       360
GTGTACGTCACTAAAACCAGCATCAAAATCCCAAGTTCTCATACCCTGATGAAAGGAGGA
 V Y V T K T S I K I P S S H T L M K G G 370       380       390       400       410       420
AGCACCAAGTATTGGTCAGGGAATTCTGAATTCCATTTTTATTCCATAAACGTTGGTGGA
 S T K Y W S G N S E F H F Y S I N V G G 430       440       450       460       470       480
TTTTTTAAGTTACGGTCTGGAGAGGAAATCAGCATCGAGGTCTCCAACCCCTCCTTACTG
 F F K L R S G E E I S I E V S N P S L L 490       500       510       520       530       540
GATCCGGATCAGGATGCAACATACTTTGGGGCTTTTAAAGTTCGAGATATAGATTGAGCC
 D P D Q D A T Y F G A F K V R D I D * (SEQ ID NO: 10)

550       560       570       580
CCAGTTTTTGGAGTGTTATGTATTTCCTGGATgcggccgc (SEQ ID NO: 14)
                                   NotI
```

Fig. 21A

```
   1  ACGTTATCGA CTGCACGGTG CACCAATGCT TCTGGCGTCA GGCAGCCATC GGAAGCTGT
  61  GTATGGCTGT GCAGGTCGTA AATCACTGCA TAATTCGTGT CGCTCAAGGC GCACTCCCGT
 121  TCTGGATAAT GTTTTTTGCG CCGACATCAT AACGGTTCTG GCAAATATTC TGAAATGAGC
 181  TGTTGACAAT TAATCATCGG CTCGTATAAT GTGTGGAATT GTGAGCGGAT AACAATTTCA
                     tac promoter
 241  CACAGGAAAC AGTATTCATG TCCCCTATAC TAGGTTATTG GAAAATTAAG GGCCTTGTGC
 301  AACCCACTCG ACTTCTTTTG GAATATCTTG AAGAAAAATA TGAAGAGCAT TTGTATGAGC
 361  GCGATGAAGG TGATAAATGG CGAAACAAAA GTTTGAATT GGGTTTGGAG TTTCCCAATC
 421  TTCCTTATTA TATTGATGGT GATGTAAAT TAACACAGTC TATGGCCATC ATACGTTATA
 481  TAGCTGACAA GCACAACATG TTGGGTGGTT GTCCAAAAGA GCGTGCAGAG ATTTCAATGC
 541  TTGAAGGAGC GGTTTTGGAT ATTAGATACG GTGTTTCGAG AATTGCATAT AGTAAAGACT
 601  TTGAAACTCT CAAAGTTGAT TTTCTTAGCA AGCTACCTGA AATGCTGAAA ATGTTCGAAG
 661  ATCGTTTATG TCATAAAACA TATTTAAATG GTGATCATGT AACCCATCCT GACTTCATGT
 721  TGTATGACGC TCTTGATGTT GTTTTATACA TGGACCCAAT GTGCCTGGAT GCGTTCCCAA
 781  AATTAGTTTG TTTTAAAAAA CGTATTGAAG CTATCCCACA AATTGATAAG TACTTGAAAT
 841  CCAGCAAGTA TATAGCATGG CCTTTGCAGG GCTGGCAAGC CACGTTTGGT GGTGGCGACC
 901  ATCCTCCAAA ATCGGATCTG GTTCCGCGTG GATCCCCAGG AATTCCCGGG TCGACTCGAG
 961  CGGCCGCATC GTGACTGACT GACGATCTGC CTCGCGCGTT TCGGTGATGA CGGTGAAAAC
1021  CTCTGACACA TGCAGCTCCC GGAGACGGTC ACAGCTTGTC TGTAAGCGGA TGCCGGGAGC
1081  AGACAAGCCC GTCAGGGCGC GTCAGCGGGT GTTGGCGGGT GTCGGGGCGC AGCCATGACC
1141  CAGTCACGTA GCGATAGCGG AGTGTATAAT TCTTGAAGAC GAAAGGGCCT CGTGATACGC
1201  CTATTTTTAT AGGTTAATGT CATGATAATA ATGGTTTCTT AGACGTCAGG TGGCACTTTT
1261  CGGGGAAATG TGCGCGGAAC CCCTATTTGT TTATTTTTCT AAATACATTC AAATATGTAT
1321  CCGCTCATGA GACAATAACC CTGATAAATG CTTCAATAAT ATTGAAAAAG GAAGAGTATG
                                                      β-lactamase initiation codon
1381  AGTATTCAAC ATTTCCGTGT CGCCCTTATT CCCTTTTTTG CGGCATTTTG CCTTCCTGTT
1441  TTTGCTCACC CAGAAACGCT GGTGAAAGTA AAAGATGCTG AAGATCAGTT GGGTGCACGA
1501  GTGGGTTACA TCGAACTGGA TCTCAACAGC GGTAAGATCC TTGAGAGTTT TCGCCCCGAA
1561  GAACGTTTTC CAATGATGAG CACTTTTAAA GTTCTGCTAT GTGGCGCGGT ATTATCCCGT
1621  GTTGACGCCG GGCAAGAGCA ACTCGGTCGC CGCATACACT ATTCTCAGAA TGACTTGGTT
1681  GAGTACTCAC CAGTCACAGA AAAGCATCTT ACGGATGGCA TGACAGTAAG AGAATTATGC
1741  AGTGCTGCCA TAACCATGAG TGATAACACT GCGGCCAACT TACTTCTGAC AACGATCGGA
1801  GGACCGAAGG AGCTAACCGC TTTTTTGCAC AACATGGGGG ATCATGTAAC TCGCCTTGAT
1861  CGTTGGGAAC CGGAGCTGAA TGAAGCCATA CCAAACGACG AGCGTGACAC CACGATGCCT
1921  GCAGCAATGG CAACAACGTT GCGCAAACTA TTAACTGGCG AACTACTTAC TCTAGCTTCC
1981  CGGCAACAAT TAATAGACTG GATGGAGGCG GATAAAGTTG CAGGACCACT TCTGCGCTCG
2041  GCCCTTCCGG CTGGCTGGTT TATTGCTGAT AAATCTGGAG CCGGTGAGCG TGGGTCTCGC
2101  GGTATCATTG CAGCACTGGG GCCAGATGGT AAGCCCTCCC GTATCGTAGT TATCTACACG
2161  ACGGGGAGTC AGGCAACTAT GGATGAACGA AATAGACAGA TCGCTGAGAT AGGTGCCTCA
2221  CTGATTAAGC ATTGGTAACT GTCAGACCAA GTTTACTCAT ATATACTTTA GATTGATTTA
                   β-lactamase termination codon
2281  AAACTTCATT TTTAATTTAA AAGGATCTAG GTGAAGATCC TTTTTGATAA TCTCATGACC
2341  AAAATCCCTT AACGTGAGTT TTCGTTCCAC TGAGCGTCAG ACCCCGTAGA AAAGATCAAA
2401  GGATCTTCTT GAGATCCTTT TTTTCTGCGC GTAATCTGCT GCTTGCAAAC AAAAAAACCA
2461  CCGCTACCAG CGGTGGTTTG TTTGCCGGAT CAAGAGCTAC CAACTCTTTT TCCGAAGGTA
2521  ACTGGCTTCA GCAGAGCGCA GATACCAAAT ACTGTCCTTC TAGTGTAGCC GTAGTTAGGC
2581  CACCACTTCA AGAACTCTGT AGCACCGCCT ACATACCTCG CTCTGCTAAT CCTGTTACCA
2641  GTGGCTGCTG CCAGTGGCGA TAAGTCGTGT CTTACCGGGT TGGACTCAAG ACGATAGTTA
```

Fig. 21B

```
2701   CCGGATAAGG CGCAGCGGTC GGGCTGAACG GGGGGTTCGT GCACACAGCC CAGCTTGGAG
2761   CGAACGACCT ACACCGAACT GAGATACCTA CAGCGTGAGC TATGAGAAAG CGCCACGCTT
2821   CCCGAAGGGA GAAAGGCGGA CAGGTATCCG GTAAGCGGCA GGGTCGGAAC AGGAGAGCGC
2881   ACGAGGGAGC TTCCAGGGGG AAACGCCTGG TATCTTTATA GTCCTGTCGG GTTTCGCCAC
2941   CTCTGACTTG AGCGTCGATT TTTGTGATGC TCGTCAGGGG GCGGAGCCT ATGGAAAAAC
3001   GCCAGCAACG CGGCCTTTTT ACGGTTCCTG GCCTTTTGCT GGCCTTTTGC TCACATGTTC
3061   TTTCCTGCGT TATCCCCTGA TTCTGTGGAT AACCGTATTA CCGCCTTTGA GTGAGCTGAT
3121   ACCGCTCGCC GCAGCCGAAC GACCGAGCGC AGCGAGTCAG TGAGCGAGGA AGCGGAAGAG
3181   CGCCTGATGC GGTATTTTCT CCTTACGCAT CTGTGCGGTA TTTCACACCG CATAAATTCC
3241   GACACCATCG AATGGTGCAA AACCTTTCGC GGTATGGCAT GATAGCGCCC GGAAGAGAGT
3301   CAATTCAGGG TGGTGAATGT GAAACCAGTA ACGTTATACG ATGTCGCAGA GTATGCCGGT
                         lacIq initiation codon
3361   GTCTCTTATC AGACCGTTTC CCGCGTGGTG AACCAGGCCA GCCACGTTTC TGCGAAAACG
3421   CGGGAAAAAG TGGAAGCGGC GATGGCGGAG CTGAATTACA TTCCCAACCG CGTGGCACAA
3481   CAACTGGCGG GCAAACAGTC GTTGCTGATT GGCGTTGCCA CCTCCAGTCT GGCCCTGCAC
3541   GCGCCGTCGC AAATTGTCGC GGCGATTAAA TCTCGCGCCG ATCAACTGGG TGCCAGCGTG
3601   GTGGTGTCGA TGGTAGAACG AAGCGGCGTC GAAGCCTGTA AAGCGGCGGT GCACAATCTT
3661   CTCGCGCAAC GCGTCAGTGG GCTGATCATT AACTATCCGC TGGATGACCA GGATGCCATT
3721   GCTGTGGAAG CTGCCTGCAC TAATGTTCCG GCGTTATTTC TTGATGTCTC TGACCAGACA
3781   CCCATCAACA GTATTATTTT CTCCCATGAA GACGGTACGC GACTGGGCGT GGAGCATCTG
3841   GTCGCATTGG GTCACCAGCA AATCGCGCTG TTAGCGGGCC CATTAAGTTC TGTCTCGGCG
3901   CGTCTGCGTC TGGCTGGCTG GCATAAATAT CTCACTCGCA ATCAAATTCA GCCGATAGCG
3961   GAACGGGAAG CGACTGGAG TGCCATGTCC GGTTTTCAAC AAACCATGCA AATGCTGAAT
4021   GAGGGCATCG TTCCCACTGC GATGCTGGTT GCCAACGATC AGATGGCGCT GGGCGCAATG
4081   CGCGCCATTA CCGAGTCCGG GCTGCGCGTT GGTGCGGATA TCTCGGTAGT GGGATACGAC
4141   GATACCGAAG ACAGCTCATG TTATATCCCG CCGTTAACCA CCATCAAACA GGATTTTCGC
4201   CTGCTGGGGC AAACCAGCGT GGACCGCTTG CTGCAACTCT CTCAGGGCCA GGCGGTGAAG
4261   GGCAATCAGC TGTTGCCCGT CTCACTGGTG AAAAGAAAAA CCACCCTGGC GCCCAATACG
4321   CAAACCGCCT CTCCCCGCGC GTTGGCCGAT TCATTAATGC AGCTGGCACG ACAGGTTTCC
4381   CGACTGGAAA GCGGGCAGTG AGCGCAACGC AATTAATGTG AGTTAGCTCA CTCATTAGGC
                         lacIq termination codon
4441   ACCCCAGGCT TTACACTTTA TGCTTCCGGC TCGTATGTTG TGTGGAATTG TGAGCGGATA
4501   ACAATTTCAC ACAGGAAACA GCTATGACCA TGATTACGGA TTCACTGGCC GTCGTTTTAC
4561   AACGTCGTGA CTGGGAAAAC CCTGGCGTTA CCCAACTTAA TCGCCTTGCA GCACATCCCC
4621   CTTTCGCCAG CTGGCGTAAT AGCGAAGAGG CCCGCACCGA TCGCCCTTCC CAACAGTTGC
4681   GCAGCCTGAA TGGCGAATGG CGCTTTGCCT GGTTTCCGGC ACCAGAAGCG GTGCCGGAAA
4741   GCTGGCTGGA GTGCGATCTT CCTGAGGCCG ATACTGTCGT CGTCCCCTCA AACTGGCAGA
4801   TGCACGGTTA CGATGCGCCC ATCTACACCA ACGTAACCTA TCCCATTACG GTCAATCCGC
4861   CGTTTGTTCC CACGGAGAAT CCGACGGGTT GTTACTCGCT CACATTTAAT GTTGATGAAA
4921   GCTGGCTACA GGAAGGCCAG ACGCGAATTA TTTTTGATGG CGTTGGAATT (SEQ ID NO: 11)
```

Position of tac promoter: 183-211
β-lactamase gene: 1,378-2,238
lacIq gene: 3,319-4,401

```
SEQUENCE LISTING

<160> NUMBER OF SEQ ID NOS: 15

<210> SEQ ID NO 1
<211> LENGTH: 2201
<212> TYPE: DNA
<213> ORGANISM: Homo sapiens
<220> FEATURE:
<221> NAME/KEY: CDS
<222> LOCATION: (129)..(1082)

<400> SEQUENCE: 1
ggccaaagcc gggctccaag tcggcgcccc acgtcgaggc tccgccgcag cctccggagt      60
tggccgcaga caagaagggg agggagcggg agagggagga gagctccgaa gcgagagggc     120 cgagcgcc atg cgc cgc gcc agc aga gac tac acc aag tac ctg cgt ggc     170
         Met Arg Arg Ala Ser Arg Asp Tyr Thr Lys Tyr Leu Arg Gly
           1               5                  10 tcg gag gag atg ggc ggc ggc ccc gga gcc ccg cac gag ggc ccc ctg     218
Ser Glu Glu Met Gly Gly Gly Pro Gly Ala Pro His Glu Gly Pro Leu
 15              20                  25                  30 cac gcc ccg ccg ccg cct gcg ccg cac cag ccc ccc gcc gcc tcc cgc     266
His Ala Pro Pro Pro Ala Pro His Gln Pro Pro Ala Ala Ser Arg
                 35                  40                  45 tcc atg ttc gtg gcc ctc ctg ggg ctg ggg ctg ggc cag gtt gtc tgc     314
Ser Met Phe Val Ala Leu Leu Gly Leu Gly Leu Gly Gln Val Val Cys
             50                  55                  60 agc gtc gcc ctg ttc ttc tat ttc aga gcg cag atg gat cct aat aga     362
Ser Val Ala Leu Phe Phe Tyr Phe Arg Ala Gln Met Asp Pro Asn Arg
         65                  70                  75
```

| | | |
|---|---|---|
| ata tca gaa gat ggc act cac tgc att tat aga att ttg aga ctc cat<br>Ile Ser Glu Asp Gly Thr His Cys Ile Tyr Arg Ile Leu Arg Leu His<br>80                       85                   90 | | 410 |
| gaa aat gca gat ttt caa gac aca act ctg gag agt caa gat aca aaa<br>Glu Asn Ala Asp Phe Gln Asp Thr Thr Leu Glu Ser Gln Asp Thr Lys<br>95                   100                105              110 | | 458 |
| tta ata cct gat tca tgt agg aga att aaa cag gcc ttt caa gga gct<br>Leu Ile Pro Asp Ser Cys Arg Arg Ile Lys Gln Ala Phe Gln Gly Ala<br>               115                     120                  125 | | 506 |
| gtg caa aag gaa tta caa cat atc gtt gga tca cag cac atc aga gca<br>Val Gln Lys Glu Leu Gln His Ile Val Gly Ser Gln His Ile Arg Ala<br>          130                   135                 140 | | 554 |
| gag aaa gcg atg gtg gat ggc tca tgg tta gat ctg gcc aag agg agc<br>Glu Lys Ala Met Val Asp Gly Ser Trp Leu Asp Leu Ala Lys Arg Ser<br>145                    150                155 | | 602 |
| aag ctt gaa gct cag cct ttt gct cat ctc act att aat gcc acc gac<br>Lys Leu Glu Ala Gln Pro Phe Ala His Leu Thr Ile Asn Ala Thr Asp<br>160                    165                170 | | 650 |
| atc cca tct ggt tcc cat aaa gtg agt ctg tcc tct tgg tac cat gat<br>Ile Pro Ser Gly Ser His Lys Val Ser Leu Ser Ser Trp Tyr His Asp<br>175                    180                185              190 | | 698 |
| cgg ggt tgg gcc aag atc tcc aac atg act ttt agc aat gga aaa cta<br>Arg Gly Trp Ala Lys Ile Ser Asn Met Thr Phe Ser Asn Gly Lys Leu<br>               195                     200                  205 | | 746 |
| ata gtt aat cag gat ggc ttt tat tac ctg tat gcc aac att tgc ttt<br>Ile Val Asn Gln Asp Gly Phe Tyr Tyr Leu Tyr Ala Asn Ile Cys Phe<br>          210                   215                 220 | | 794 |
| cga cat cat gaa act tca gga gac cta gct aca gag tat ctt caa cta<br>Arg His His Glu Thr Ser Gly Asp Leu Ala Thr Glu Tyr Leu Gln Leu<br>225                    230                235 | | 842 |
| atg gtg tac gtc act aaa acc agc atc aaa atc cca agt tct cat acc<br>Met Val Tyr Val Thr Lys Thr Ser Ile Lys Ile Pro Ser Ser His Thr<br>240                    245                250 | | 890 |
| ctg atg aaa gga gga agc acc aag tat tgg tca ggg aat tct gaa ttc<br>Leu Met Lys Gly Gly Ser Thr Lys Tyr Trp Ser Gly Asn Ser Glu Phe<br>255                    260                265              270 | | 938 |
| cat ttt tat tcc ata aac gtt ggt gga ttt ttt aag tta cgg tct gga<br>His Phe Tyr Ser Ile Asn Val Gly Gly Phe Phe Lys Leu Arg Ser Gly<br>                    275                   280                285 | | 986 |
| gag gaa atc agc atc gag gtc tcc aac ccc tcc tta ctg gat ccg gat<br>Glu Glu Ile Ser Ile Glu Val Ser Asn Pro Ser Leu Leu Asp Pro Asp<br>          290                   295                 300 | | 1034 |
| cag gat gca aca tac ttt ggg gct ttt aaa gtt cga gat ata gat tga<br>Gln Asp Ala Thr Tyr Phe Gly Ala Phe Lys Val Arg Asp Ile Asp<br>               305                    310                315 | | 1082 |
| gccccagttt tggagtgtt atgtatttcc tggatgtttg gaaacatttt ttaaaacaag | | 1142 |
| ccaagaaaga tgtatatagg tgtgtgagac tactaagagg catggcccca acggtacacg | | 1202 |
| actcagtatc catgctcttg accttgtaga gaacacgcgt atttacctgc cagtgggaga | | 1262 |
| tgttagactc atggtgtgtt acacaatggt ttttaaattt tgtaatgaat tcctagaatt | | 1322 |
| aaaccagatt ggagcaatta cgggttgacc ttatgagaaa ctgcatgtgg gctatggag | | 1382 |
| gggttggtcc ctggtcatgt gccccttcgc agctgaagtg gagagggtgt catctagcgc | | 1442 |
| aattgaagga tcatctgaag gggcaaattc ttttgaattg ttacatcatg ctggaacctg | | 1502 |
| caaaaaatac ttttctaat gaggagagaa aatatatgta tttttatata atatctaaag | | 1562 |
| ttatatttca gatgtaatgt tttctttgca agtattgta aattatattt gtgctatagt | | 1622 |
| atttgattca aaatatttaa aaatgtcttg ctgttgacat atttaatgtt ttaaatgtac | | 1682 |

-continued

```
agacatattt aactggtgca ctttgtaaat tccctgggga aaacttgcag ctaaggaggg    1742
gaaaaaaatg ttgtttccta atatcaaatg cagtatattt cttcgttctt tttaagttaa    1802 tagattttttt cagacttgtc aagcctgtgc aaaaaaatta aaatggatgc cttgaataat   1862
aagcaggatg ttggccacca ggtgcctttc aaatttagaa actaattgac tttagaaagc    1922
tgacattgcc aaaaggata cataatgggc cactgaaatt tgtcaagagt agttatataa     1982
ttgttgaaca ggtgttttc cacaagtgcc gcaaattgta cctttttttt ttttcaaaa      2042 tagaaaagtt attagtggtt tatcagcaaa aaagtccaat tttaatttag taaatgttat    2102
tttatactgt acaataaaaa cattgccttt gaatgttaat ttttggtac aaaaataaat    2162 ttatatgaaa aaaaaaaaaa aaaaaaaaaa aaaaaaaa                            2201
```

<210> SEQ ID NO 2
<211> LENGTH: 317
<212> TYPE: PRT
<213> ORGANISM: Homo sapiens

<400> SEQUENCE: 2

```
Met Arg Arg Ala Ser Arg Asp Tyr Thr Lys Tyr Leu Arg Gly Ser Glu
  1               5                  10                  15

Glu Met Gly Gly Gly Pro Gly Ala Pro His Glu Gly Pro Leu His Ala
             20                  25                  30

Pro Pro Pro Ala Pro His Gln Pro Pro Ala Ala Ser Arg Ser Met
         35                  40                  45

Phe Val Ala Leu Leu Gly Leu Gly Leu Gly Gln Val Val Cys Ser Val
     50                  55                  60

Ala Leu Phe Phe Tyr Phe Arg Ala Gln Met Asp Pro Asn Arg Ile Ser
 65                  70                  75                  80

Glu Asp Gly Thr His Cys Ile Tyr Arg Ile Leu Arg Leu His Glu Asn
                 85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
            115                 120                 125

Lys Glu Leu Gln His Ile Val Gly Ser Gln His Ile Arg Ala Glu Lys
        130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285
```

```
Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315

<210> SEQ ID NO 3
<211> LENGTH: 1275
<212> TYPE: DNA
<213> ORGANISM: Artificial Sequence
<220> FEATURE:
<223> OTHER INFORMATION: Description of Artificial Sequence: GST-RANKL
      (aa127-317)

<400> SEQUENCE: 3 atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggcctttgc agggctggca agccacgttt ggtggtggcg accatcctcc aaaatcggat     660
ctggttccgc gtggatcccc aggaattccc gggtcgactg tgcaaaagga attacaacat     720
atcgttggat cacagcacat cagagcgagg aaagcgatgg tggatggctc atggttagat     780
ctggccaaga ggagcaagct tgaagctcag cctttgctc atctcactat taatgccacc     840
gacatcccat ctggttccca taaagtgagt ctgtcctctt ggtaccatga tcggggttgg     900
gccaagatct ccaacatgac ttttagcaat ggaaaactaa tagttaatca ggatggcttt     960
tattacctgt atgccaacat ttgctttcga catcatgaaa cttcaggaga cctagctaca    1020
gagtatcttc aactaatggt gtacgtcact aaaaccagca tcaaaatccc aagttctcat    1080
accctgatga aggaggaag caccaagtat tggtcaggga attctgaatt ccatttttat    1140
tccataaacg ttggtggatt ttttaagtta cggtctggag aggaaatcag catcgaggtc    1200 tccaaccct ccttactgga tccggatcag gatgcaacat actttggggc ttttaaagtt    1260
cgagatatag attga                                                    1275

<210> SEQ ID NO 4
<211> LENGTH: 442
<212> TYPE: PRT
<213> ORGANISM: Artificial Sequence
<220> FEATURE:
<223> OTHER INFORMATION: Description of Artificial Sequence: GST-RANKL
      (aa127-317)

<400> SEQUENCE: 4

Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
```

```
                   35                  40                  45
Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Leu Val
225                 230                 235                 240

Pro Arg Gly Ser Pro Gly Ile Pro Gly Ser Thr Val Gln Lys Glu Leu
                245                 250                 255

Gln His Ile Val Gly Ser Gln His Ile Arg Ala Glu Lys Ala Met Val
            260                 265                 270

Asp Gly Ser Trp Leu Asp Leu Ala Lys Arg Ser Lys Leu Glu Ala Gln
        275                 280                 285

Pro Phe Ala His Leu Thr Ile Asn Ala Thr Asp Ile Pro Ser Gly Ser
    290                 295                 300

His Lys Val Ser Leu Ser Ser Trp Tyr His Asp Arg Gly Trp Ala Lys
305                 310                 315                 320

Ile Ser Asn Met Thr Phe Ser Asn Gly Lys Leu Ile Val Asn Gln Asp
                325                 330                 335

Gly Phe Tyr Tyr Leu Tyr Ala Asn Ile Cys Phe Arg His His Glu Thr
            340                 345                 350

Ser Gly Asp Leu Ala Thr Glu Tyr Leu Gln Leu Met Val Tyr Val Thr
        355                 360                 365

Lys Thr Ser Ile Lys Ile Pro Ser Ser His Thr Leu Met Lys Gly Gly
    370                 375                 380

Ser Thr Lys Tyr Trp Ser Gly Asn Ser Glu Phe His Phe Tyr Ser Ile
385                 390                 395                 400

Asn Val Gly Gly Phe Phe Lys Leu Arg Ser Gly Glu Glu Ile Ser Ile
                405                 410                 415

Glu Val Ser Asn Pro Ser Leu Leu Asp Pro Asp Gln Asp Ala Thr Tyr
            420                 425                 430

Phe Gly Ala Phe Lys Val Arg Asp Ile Asp
        435                 440

<210> SEQ ID NO 5
<211> LENGTH: 1236
```

```
<212> TYPE: DNA
<213> ORGANISM: Artificial Sequence
<220> FEATURE:
<223> OTHER INFORMATION: Description of Artificial Sequence: GST-RANKL
      (aa140-317)

<400> SEQUENCE: 5
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttccca atcttcctta ttatattgat      180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600
tggcctttgc agggctggca agccacgttt ggtggtggcg accatcctcc aaaatcggat     660
ctggttccgc gtggatcccc aggaattccc gggtcgacta tcagagcaga gaaagcgatg     720
gtggatggct catggttaga tctggccaag aggagcaagc ttgaagctca gccttttgct     780
catctcacta ttaatgccac cgacatccca tctggttccc ataaagtgag tctgtcctct     840
tggtaccatg atcggggttg ggccaagatc tccaacatga cttttagcaa tggaaaacta     900
atagttaatc aggatggctt ttattacctg tatgccaaca tttgctttcg acatcatgaa     960
acttcaggag acctagctac agagtatctt caactaatgg tgtacgtcac taaaaccagc    1020
atcaaaatcc caagttctca taccctgatg aaaggaggaa gcaccaagta ttggtcaggg    1080
aattctgaat ccatttttta ttccataaac gttggtggat ttttaagtt acggtctgga     1140
gaggaaatca gcatcgaggt ctccaacccc tccttactgg atccggatca ggatgcaaca    1200
tactttgggg cttttaaagt tcgagatata gattga                             1236

<210> SEQ ID NO 6
<211> LENGTH: 429
<212> TYPE: PRT
<213> ORGANISM: Artificial Sequence
<220> FEATURE:
<223> OTHER INFORMATION: Description of Artificial Sequence: GST-RANKL
      (aa140-317)

<400> SEQUENCE: 6

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
```

|   |   |   |   |   | 100 |   |   |   |   | 105 |   |   |   |   | 110 |   |   |
|---|---|---|---|---|---|---|---|---|---|---|---|---|---|---|---|---|---|
| Lys | Asp | Phe | Glu | Thr | Leu | Lys | Val | Asp | Phe | Leu | Ser | Lys | Leu | Pro | Glu |   |   |
|   |   |   |   | 115 |   |   |   |   | 120 |   |   |   |   | 125 |   |   |   |

Lys Asp Phe Glu Thr Leu Lys Val Asp Phe Leu Ser Lys Leu Pro Glu
         115                120                125

Met Leu Lys Met Phe Glu Asp Arg Leu Cys His Lys Thr Tyr Leu Asn
  130                   135                140

Gly Asp His Val Thr His Pro Asp Phe Met Leu Tyr Asp Ala Leu Asp
145                  150                155                160

Val Val Leu Tyr Met Asp Pro Met Cys Leu Asp Ala Phe Pro Lys Leu
                165                170                175

Val Cys Phe Lys Lys Arg Ile Glu Ala Ile Pro Gln Ile Asp Lys Tyr
        180                185                190

Leu Lys Ser Ser Lys Tyr Ile Ala Trp Pro Leu Gln Gly Trp Gln Ala
        195                200                205

Thr Phe Gly Gly Gly Asp His Pro Pro Lys Ser Asp Leu Val Pro Arg
      210                215                220

Gly Ser Pro Gly Ile Pro Gly Ser Thr Arg Ala Ala Ser Leu Val
225                  230                235                240

Pro Arg Gly Ser Pro Gly Ile Pro Gly Ser Thr Ile Arg Ala Glu Lys
        245                250                255

Ala Met Val Asp Gly Ser Trp Leu Asp Leu Ala Lys Arg Ser Lys Leu
            260                265                270

Glu Ala Gln Pro Phe Ala His Leu Thr Ile Asn Ala Thr Asp Ile Pro
        275                280                285

Ser Gly Ser His Lys Val Ser Leu Ser Ser Trp Tyr His Asp Arg Gly
      290                295                300

Trp Ala Lys Ile Ser Asn Met Thr Phe Ser Asn Gly Lys Leu Ile Val
305                  310                315                320

Asn Gln Asp Gly Phe Tyr Tyr Leu Tyr Ala Asn Ile Cys Phe Arg His
            325                330                335

His Glu Thr Ser Gly Asp Leu Ala Thr Glu Tyr Leu Gln Leu Met Val
            340                345                350

Tyr Val Thr Lys Thr Ser Ile Lys Ile Pro Ser Ser His Thr Leu Met
        355                360                365

Lys Gly Gly Ser Thr Lys Tyr Trp Ser Gly Asn Ser Glu Phe His Phe
      370                375                380

Tyr Ser Ile Asn Val Gly Gly Phe Phe Lys Leu Arg Ser Gly Glu Glu
385                  390                395                400

Ile Ser Ile Glu Val Ser Asn Pro Ser Leu Leu Asp Pro Asp Gln Asp
            405                410                415

Ala Thr Tyr Phe Gly Ala Phe Lys Val Arg Asp Ile Asp
        420                425

<210> SEQ ID NO 7
<211> LENGTH: 1179
<212> TYPE: DNA
<213> ORGANISM: Artificial Sequence
<220> FEATURE:
<223> OTHER INFORMATION: Description of Artificial Sequence: GST-RANKL
     (aa159-317)

<400> SEQUENCE: 7
atgtccccta ctactaggtta ttggaaaatt aagggccttg tgcaacccac tcgacttctt     60
ttggaatatc ttgaagaaaa atatgaagag catttgtatg agcgcgatga aggtgataaa    120
tggcgaaaca aaaagtttga attggggtttg gagtttccca atcttcctta ttatattgat    180
ggtgatgtta aattaacaca gtctatggcc atcatacgtt atatagctga caagcacaac    240

```
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg atgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatcccc aggaattccc gggtcgacta agcttgaagc tcagccttt    720 gctcatctca ctattaatgc caccgacatc ccatctggtt cccataaagt gagtctgtcc    780
tcttggtacc atgatcgggg ttgggccaag atctccaaca tgactttag caatggaaaa    840 ctaatagtta atcaggatgg cttttattac ctgtatgcca catttgctt cgacatcat    900 gaaacttcag agacctagc tacagagtat cttcaactaa tggtgtacgt cactaaaacc    960
agcatcaaaa tcccaagttc tcataccctg atgaaggag gaagcaccaa gtattggtca   1020
gggaattctg aattccattt ttattccata acgttggtg gatttttaa gttacggtct   1080 ggagaggaaa tcagcatcga ggtctccaac ccctccttac tggatccgga tcaggatgca   1140
acatactttg gggcttttaa agttcgagat atagattga                          1179
```

<210> SEQ ID NO 8
<211> LENGTH: 410
<212> TYPE: PRT
<213> ORGANISM: Artificial Sequence
<220> FEATURE:
<223> OTHER INFORMATION: Description of Artificial Sequence: GST-RANKL
    (aa159-317)

<400> SEQUENCE: 8

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

```
Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Leu Val
225                 230                 235                 240

Pro Arg Gly Ser Pro Gly Ile Pro Gly Ser Thr Lys Leu Glu Ala Gln
                245                 250                 255

Pro Phe Ala His Leu Thr Ile Asn Ala Thr Asp Ile Pro Ser Gly Ser
                260                 265                 270

His Lys Val Ser Leu Ser Ser Trp Tyr His Asp Arg Gly Trp Ala Lys
            275                 280                 285

Ile Ser Asn Met Thr Phe Ser Asn Gly Lys Leu Ile Val Asn Gln Asp
        290                 295                 300

Gly Phe Tyr Tyr Leu Tyr Ala Asn Ile Cys Phe Arg His His Glu Thr
305                 310                 315                 320

Ser Gly Asp Leu Ala Thr Glu Tyr Leu Gln Leu Met Val Tyr Val Thr
                325                 330                 335

Lys Thr Ser Ile Lys Ile Pro Ser Ser His Thr Leu Met Lys Gly Gly
            340                 345                 350

Ser Thr Lys Tyr Trp Ser Gly Asn Ser Glu Phe His Phe Tyr Ser Ile
        355                 360                 365

Asn Val Gly Gly Phe Phe Lys Leu Arg Ser Gly Glu Glu Ile Ser Ile
    370                 375                 380

Glu Val Ser Asn Pro Ser Leu Leu Asp Pro Asp Gln Asp Ala Thr Tyr
385                 390                 395                 400

Phe Gly Ala Phe Lys Val Arg Asp Ile Asp
                405                 410

<210> SEQ ID NO 9
<211> LENGTH: 587
<212> TYPE: DNA
<213> ORGANISM: Artificial Sequence
<220> FEATURE:
<223> OTHER INFORMATION: Description of Artificial Sequence: Synthetic

<400> SEQUENCE: 9
gtcgactatc agagcagaga aagcgatggt ggatggctca tggttagatc tggccaagag      60
gagcaagctt gaagctcagc cttttgctca tctcactatt aatgccaccg acatcccatc     120
tggttcccat aaagtgagtc tgtcctcttg gtaccatgat cggggttggg ccaagatctc     180
caacatgact tttagcaatg gaaaactaat agttaatcag gatggctttt attacctgta     240
tgccaacatt tgctttcgac atcatgaaac ttcaggagac ctagctacag agtatcttca     300
actaatggtg tacgtcacta aaaccagcat caaaatccca agttctcata ccctgatgaa     360
aggaggaagc accaagtatt ggtcaggaa ttctgaattc cattttt att ccataaacgt     420 tggtggattt tttaagttac ggtctggaga ggaaatcagc atcgaggtct ccaacccctc     480
cttactggat ccggatcagg atgcaacata ctttggggct tttaaagttc gagatataga     540
ttgagcccca gttttggag tgttatgtat ttcctggatg cggccgc                    587

<210> SEQ ID NO 10
<211> LENGTH: 178
<212> TYPE: PRT
<213> ORGANISM: Artificial Sequence
<220> FEATURE:
<223> OTHER INFORMATION: Description of Artificial Sequence: Synthetic
```

<400> SEQUENCE: 10

```
Ile Arg Ala Glu Lys Ala Met Val Asp Gly Ser Trp Leu Asp Leu Ala
  1               5                  10                  15
Lys Arg Ser Lys Leu Glu Ala Gln Pro Phe Ala His Leu Thr Ile Asn
             20                  25                  30
Ala Thr Asp Ile Pro Ser Gly Ser His Lys Val Ser Leu Ser Ser Trp
         35                  40                  45
Tyr His Asp Arg Gly Trp Ala Lys Ile Ser Asn Met Thr Phe Ser Asn
     50                  55                  60
Gly Lys Leu Ile Val Asn Gln Asp Gly Phe Tyr Tyr Leu Tyr Ala Asn
 65                  70                  75                  80
Ile Cys Phe Arg His His Glu Thr Ser Gly Asp Leu Ala Thr Glu Tyr
             85                  90                  95
Leu Gln Leu Met Val Tyr Val Thr Lys Thr Ser Ile Lys Ile Pro Ser
            100                 105                 110
Ser His Thr Leu Met Lys Gly Gly Ser Thr Lys Tyr Trp Ser Gly Asn
            115                 120                 125
Ser Glu Phe His Phe Tyr Ser Ile Asn Val Gly Gly Phe Phe Lys Leu
        130                 135                 140
Arg Ser Gly Glu Glu Ile Ser Ile Glu Val Ser Asn Pro Ser Leu Leu
145                 150                 155                 160
Asp Pro Asp Gln Asp Ala Thr Tyr Phe Gly Ala Phe Lys Val Arg Asp
                165                 170                 175
Ile Asp
```

<210> SEQ ID NO 11
<211> LENGTH: 4970
<212> TYPE: DNA
<213> ORGANISM: Artificial Sequence
<220> FEATURE:
<223> OTHER INFORMATION: Description of Artificial Sequence: Synthetic

<400> SEQUENCE: 11

```
acgttatcga ctgcacggtg caccaatgct tctggcgtca ggcagccatc ggaagctgtg      60
gtatggctgt gcaggtcgta aatcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattcatg tcccctatac taggttattg gaaaattaag gccttgtgc      300
aacccactcg acttcttttg gaatatcttg aagaaaaata tgaagagcat ttgtatgagc     360
gcgatgaagg tgataaatgg cgaaacaaaa agtttgaatt gggtttggag tttcccaatc     420
ttccttatta tattgatggt gatgttaaat aacacagtc tatggccatc atacgttata     480
tagctgacaa gcacaacatg ttgggtggtt gtccaaaaga gcgtgcagag atttcaatgc     540
ttgaaggagc ggttttggat attagatacg gtgtttcgag aattgcatat agtaaagact     600
ttgaaactct caaagttgat tttcttagca agctacctga atgctgaaa atgttcgaag     660
atcgtttatg tcataaaaca tatttaaatg gtgatcatgt aacccatcct gacttcatgt     720
tgtatgacgc tcttgatgtt gttttataca tggacccaat gtgcctggat gcgttcccaa     780
aattagtttg ttttaaaaaa cgtattgaag ctatcccaca aattgataag tacttgaaat     840
ccagcaagta tatagcatgg cctttgcagg gctggcaagc cacgtttggt ggtggcgacc     900
atcctccaaa atcggatctg gttccgcgtg atccccagg aattcccggg tcgactcgag     960
cggccgcatc gtgactgact gacgatctgc ctcgcgcgtt tcggtgatga cggtgaaaac    1020
```

```
ctctgacaca tgcagctccc ggagacggtc acagcttgtc tgtaagcgga tgccgggagc    1080
agacaagccc gtcagggcgc gtcagcgggt gttggcgggt gtcggggcgc agccatgacc    1140
cagtcacgta gcgatagcgg agtgtataat tcttgaagac gaaagggcct cgtgatacgc    1200
ctattttat aggttaatgt catgataata atggtttctt agacgtcagg tggcacttt     1260
cggggaaatg tgcgcggaac ccctatttgt ttattttct aaatacattc aaatatgtat    1320
ccgctcatga gacaataacc ctgataaatg cttcaataat attgaaaaag gaagagtatg    1380
agtattcaac atttccgtgt cgcccttatt ccctttttg cggcattttg ccttcctgtt    1440
tttgctcacc cagaaacgct ggtgaaagta aaagatgctg aagatcagtt gggtgcacga    1500
gtgggttaca tcgaactgga tctcaacagc ggtaagatcc ttgagagttt tcgccccgaa    1560
gaacgttttc caatgatgag cacttttaaa gttctgctat gtggcgcggt attatcccgt    1620
gttgacgccg ggcaagagca actcggtcgc cgcatacact attctcagaa tgacttggtt    1680
gagtactcac cagtcacaga aaagcatctt acggatggca tgacagtaag agaattatgc    1740
agtgctgcca taaccatgag tgataacact gcggccaact tacttctgac aacgatcgga    1800
ggaccgaagg agctaaccgc ttttttgcac aacatggggg atcatgtaac tcgccttgat    1860
cgttgggaac cggagctgaa tgaagccata ccaaacgacg agcgtgacac cacgatgcct    1920
gcagcaatgg caacaacgtt gcgcaaacta ttaactggcg aactacttac tctagcttcc    1980
cggcaacaat taatagactg gatggaggcg gataaagttg caggaccact tctgcgctcg    2040
gcccttccgg ctggctggtt tattgctgat aaatctggag ccggtgagcg tgggtctcgc    2100
ggtatcattg cagcactggg gccagatggt aagccctccc gtatcgtagt tatctacacg    2160
acggggagtc aggcaactat ggatgaacga atagacaga tcgctgagat aggtgcctca    2220
ctgattaagc attggtaact gtcagaccaa gtttactcat atatacttta gattgattta    2280
aaacttcatt tttaatttaa aaggatctag gtgaagatcc tttttgataa tctcatgacc    2340
aaaatccctt aacgtgagtt ttcgttccac tgagcgtcag accccgtaga aagatcaaa    2400
ggatcttctt gagatccttt ttttctgcgc gtaatctgct gcttgcaaac aaaaaaacca    2460
ccgctaccag cggtggtttg tttgccggat caagagctac caactctttt tccgaaggta    2520
actggcttca gcagagcgca gataccaaat actgtccttc tagtgtagcc gtagttaggc    2580
caccacttca agaactctgt agcaccgcct acatacctcg ctctgctaat cctgttacca    2640
gtggctgctg ccagtggcga taagtcgtgt cttaccgggt tggactcaag acgatagtta    2700
ccggataagg cgcagcggtc gggctgaacg gggggttcgt gcacacagcc cagcttggag    2760
cgaacgacct acaccgaact gagatacta cagcgtgagc tatgagaaag cgccacgctt    2820
cccgaaggga gaaaggcgga caggtatccg gtaagcggca gggtcggaac aggagagcgc    2880
acgagggagc ttccaggggg aaacgcctgg tatctttata gtcctgtcgg gtttcgccac    2940
ctctgacttg agcgtcgatt tttgtgatgc tcgtcagggg ggcggagcct atggaaaaac    3000
gccagcaacg cggccttttt acggttcctg gccttttgct ggccttttgc tcacatgttc    3060
tttcctgcgt tatcccctga ttctgtggat aaccgtatta ccgcctttga gtgagctgat    3120
accgctcgcc gcagccgaac gaccgagcgc agcgagtcag tgagcgagga agcggaagag    3180
cgcctgatgc ggtattttct ccttacgcat ctgtgcggta tttcacaccg cataaattcc    3240
gacaccatcg aatggtgcaa aacctttcgc ggtatggcat gatagcgccc ggaagagagt    3300
caattcaggt tggtgaatgt gaaaccagta acgttatacg atgtcgcaga gtatgccggt    3360
gtctcttatc agaccgtttc ccgcgtggtg aaccaggcca gccacgtttc tgcgaaaacg    3420
```

-continued

```
cgggaaaaag tggaagcggc gatggcggag ctgaattaca ttcccaaccg cgtggcacaa    3480
caactggcgg gcaaacagtc gttgctgatt ggcgttgcca cctccagtct ggccctgcac    3540
gcgccgtcgc aaattgtcgc ggcgattaaa tctcgcgccg atcaactggg tgccagcgtg    3600
gtggtgtcga tggtagaacg aagcggcgtc gaagcctgta aagcggcggt gcacaatctt    3660
ctcgcgcaac gcgtcagtgg gctgatcatt aactatccgc tggatgacca ggatgccatt    3720
gctgtggaag ctgcctgcac taatgttccg gcgttatttc ttgatgtctc tgaccagaca    3780
cccatcaaca gtattatttt ctcccatgaa gacggtacgc gactgggcgt ggagcatctg    3840
gtcgcattgg gtcaccagca aatcgcgctg ttagcgggcc cattaagttc tgtctcggcg    3900
cgtctgcgtc tggctggctg gcataaatat ctcactcgca atcaaattca gccgatagcg    3960
gaacgggaag gcgactggag tgccatgtcc ggttttcaac aaaccatgca aatgctgaat    4020
gagggcatcg ttcccactgc gatgctggtt gccaacgatc agatggcgct gggcgcaatg    4080
cgcgccatta ccgagtccgg gctgcgcgtt ggtgcggata tctcggtagt gggatacgac    4140
gataccgaag acagctcatg ttatatcccg ccgttaacca ccatcaaaca ggattttcgc    4200
ctgctggggc aaaccagcgt ggaccgcttg ctgcaactct ctcagggcca ggcggtgaag    4260
ggcaatcagc tgttgcccgt ctcactggtg aaaagaaaaa ccaccctggc gcccaatacg    4320
caaaccgcct ctccccgcgc gttggccgat tcattaatgc agctggcacg acaggtttcc    4380
cgactggaaa gcgggcagtg agcgcaacgc aattaatgtg agttagctca ctcattaggc    4440
acccaggct ttacactta tgcttccggc tcgtatgttg tgtggaattg tgagcggata    4500
acaatttcac acaggaaaca gctatgacca tgattacgga ttcactggcc gtcgttttac    4560
aacgtcgtga ctgggaaaac cctggcgtta cccaacttaa tcgccttgca gcacatcccc    4620
ctttcgccag ctggcgtaat agcgaagagg cccgcaccga tcgcccttcc caacagttgc    4680
gcagcctgaa tggcgaatgg cgctttgcct ggtttccggc accagaagcg gtgccggaaa    4740
gctggctgga gtgcgatctt cctgaggccg atactgtcgt cgtcccctca aactggcaga    4800
tgcacggtta cgatgcgccc atctacacca acgtaaccta tcccattacg gtcaatccgc    4860
cgtttgttcc cacggagaat ccgacgggtt gttactcgct cacatttaat gttgatgaaa    4920
gctggctaca ggaaggccag acgcgaatta ttttgatgg cgttggaatt    4970
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: CpG
      oligonucleotide

<400> SEQUENCE: 12

```
tccatgacgt tcctgatgct                                                  20
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: GpC
      oligonucleotide

<400> SEQUENCE: 13

```
tccatgagct tcctgatgct                                                  20
```

```
<210> SEQ ID NO 14
<211> LENGTH: 587
<212> TYPE: DNA
<213> ORGANISM: Artificial Sequence
<220> FEATURE:
<223> OTHER INFORMATION: Description of Artificial Sequence: Synthetic

<400> SEQUENCE: 14
gtcgactatc agagcagaga aagcgatggt ggatggctca tggttagatc tggccaagag      60
gagcaagctt gaagctcagc cttttgctca tctcactatt aatgccaccg acatcccatc     120
tggttcccat aaagtgagtc tgtcctcttg gtaccatgat cggggttggg ccaagatctc     180
caacatgact tttagcaatg gaaaactaat agttaatcag gatggctttt attacctgta     240
tgccaacatt tgctttcgac atcatgaaac ttcaggagac ctagctacag agtatcttca     300
actaatggtg tacgtcacta aaaccagcat caaaatccca agttctcata ccctgatgaa     360
aggaggaagc accaagtatt ggtcagggaa ttctgaattc cattttattt ccataaacgt     420
tggtggattt tttaagttac ggtctggaga ggaaatcagc atcgaggtct ccaaccccctc    480 cttactggat ccggatcagg atgcaacata ctttggggct tttaaagttc gagatataga    540
ttgagcccca gtttttggag tgttatgtat ttcctggatg cggccgc                   587

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic

<400> SEQUENCE: 15
ctggttccgc gtggatcccc aggaattccc gggtcgactc gagcggccgc atcgtga       57
```

DETECTION OF INFLAMMATORY DISEASE AND COMPOSITION FOR PREVENTION OR TREATMENT OF INFLAMMATORY DISEASE

TECHNICAL FIELD

The present invention relates to a method for diagnosing or suppressing inflammatory diseases such as sepsis, allergies, and autoimmune diseases with the use of RANKL, which suppresses the production of inflammatory cytokines or improves the survival rate of an inflammatory animal model.

BACKGROUND ART

In recent years, it is known even in surgical fields that humoral factors produced at excessive levels play important roles in formation of pathological conditions during the perioperative period of significantly invasive surgery or the acute phase of a medical emergency such as an infectious disease. It is extremely important to measure various humoral factors in order to gain early, comprehensive knowledge of a pathology that changes every day or every second under such invasion and to apply the understanding clinically. Studies concerning various humoral factors in the process of shifts from sepsis to multiple organ dysfunction syndrome (MODS, by which the functions of a plurality of organs are damaged) have drastically progressed together with the development of molecular biological techniques. Recent studies on MODS have been improved to indicate a study approach that involves analyzing the mechanism of damage at the cellular level and microenvironment or humoral factors, so as to get closer to the pathology. Specifically, based on the understanding that MODS cases are extremely analogous to each other in terms of onset mechanism or pathology even if the causes of MODS cases differ (e.g., an MODS case due to sepsis), the control of factors involved in the shift to pathology that is developed much earlier before the onset of MODS has recently been emphasized. It can be said that clinicians and researchers are currently focusing on elucidation of the pathology of sepsis that occurs at the prestage of MODS and establishment of effective countermeasures against the pathology rather on treatment for MODS itself.

Humoral factors are useful as inflammatory markers. Specifically, CRP (C-reactive protein), TNF-α, IL-1, IL-6, IL-8, IL-10, MIP-1, HMGB-1, MIF, C5a, calcitonin, and the like are known (Marshall et al., Crit Care Med 31: 1560, 2003). It has been reported concerning CRP such that CRP is used in combination with the number of platelets or the like for evaluation of the prognosis of severe sepsis (Asayama et al., Keio J Med 47: 19 1998). It has also been reported that no significant differences are confirmed between sepsis and trauma (Endo et al., Journal of Infection 73: 197 1999). Hence, solid evaluation has not been established for CRP. Similarly, in the case of TNF-α or IL-6, while it has been reported that no significant differences have been confirmed between sepsis and trauma (Endo et al., Journal of Infection 73: 197 1999), it has also been reported that IL-6 is used as a prognosis marker for sepsis (Reinhart et al., Crit Care Med 29: 765, 2001). Thus, solid evaluation has not been established for TNF-α or IL-6. Moreover, it has been reported that IL-10 is effective (Ono et al., Am J Surg 188: 150, 2004), however, it cannot be said that the effects of IL-10 have been sufficiently verified through use. Involvement of MIF in acute respiratory distress syndrome (ARSD), bronchial asthma, or the like has been reported (Donnelly et al., Nat Med 3: 320, 1997; Rossi et al., J Clin Invest 101: 2869, 1998), but it is unknown whether or not MIF can be used as a marker. It has not been revealed if the above-mentioned humoral factors cause sepsis or are produced as a result of sepsis.

Inflammatory reactions are biological reactions that limit the spreading of damage to a living body due to invasion and repair such damage. They occur as nonspecific reactions against all injuries or invasions. Inflammatory reactions are actually physiological biological reactions that take place in close association with neuroendocrine reactions, immunoinflammatory reactions, and coagulation-fibrolysis reactions. Inflammatory reactions are expressed locally in the forms of flare, swelling, pain, heat, and the like, and they cause systemic reactions with fever, tachycardia, tachypnea, and increased number of leukocytes when invasion is significant. Such conditions are referred to as systemic inflammatory response syndrome (SIRS). Examples thereof include SIRS not associated with infection or the like, but rather with trauma, burn, pancreatitis, and states after significantly invasive surgery, as well as SIRS associated with infection due to bacteria, fungi, parasites, viruses, or the like. In particular, SIRS caused by infection is referred to as sepsis.

Inflammatory reactions are established by vasodilation, vascular hyperpermeability, leukocyte-vascular endothelial cell activation, or the like. These reactions are induced by complements, amine, kinin, prostanoid, cytokine, and thrombin that are nonspecifically produced as invasion proceeds. Localized inflammatory reactions are induced by local noxious stimuli. However, when biological invasion is significant, systemic escape of these inflammatory mediators (and in particular, cytokine and thrombin) takes place and then systemic vasodilation, hyperpermeability, and leukocyte-vascular endothelial cell activation are observed. Inflammatory reaction has stages of receipt of noxious stimuli, reaction, and repairment. When a systemic inflammatory reaction is sustained, the reaction does not reach the repairment stage, so that biological homeostasis fails. In such case, it is known that MODS is induced to lead the living body to death.

For defense against invasion in the living body, three systems, the nervous system, the endocrine system, and the immune system, undergo reactions while closely interacting with each other. The nervous and endocrine systems are activated as invasion proceeds, resulting in enhanced energy metabolism, gluconeogenesis, increased cardiac output, and the like. Thus, inflammatory reactions are systemically enhanced. Meanwhile, cortisol is known to suppress the immune system and catecholamine is known to suppress the activity of NK cells or killer T cells, which are immunocytes. Bacterial infection or the occurrence of tissue damage activates the complement system or the blood coagulation system, along with which vascular endothelial cells are activated and phagocytic cells including monocytes, macrophages, and neutrophils migrate. Thus, inflammatory cytokines (composed mainly of TNF-α and IL-1) are freed from the damaged sites. With liberation of these inflammatory cytokines, protease or active oxygen, platelet-activating factors, and the like are also freed, forming the pathology of SIRS. Therefore, it is possible to consider that SIRS is also a pathological condition caused by hypercytokinemia (Riedemann et al., Nat Med 9: 517, 2003).

It has been reported that in the U.S. that about 750,000 persons are affected with sepsis yearly and 210,000 or more persons lose their lives due to sepsis (Wheeler et al., N Engl J Med 340: 207, 1999; Severansky et al., Sepsis 3: 11, 1999; Hotchkiss et al., N Engl J Med 348: 138, 2003). Furthermore, treatment for sepsis causes significant economic impact because of lengthy ICU hospital stays or increased amounts of resources used. However, although establishment of a therapeutic method against sepsis that is also referred to as high inflammatory cytokinemia has been attempted as an emergent issue throughout the world, no therapeutic method currently exists by which reduction of sepsis fatalities can be realized (Vincent et al., Clin Infect Dis 34: 1084, 2002). A therapeutic method has been reported recently by which significant improvement in the prognosis of severe sepsis can be achieved via administration of activated protein C (APC) (Bernard et al., N Engl J Med 344: 699, 2001). APC will be approved by the U.S. Food and Drug Administration (FDA) for the first time as a therapeutic agent against severe sepsis. However, the degree of effectiveness of APC is a slight rise in lifesaving rate of only approximately 6%-7%. Thus, sepsis is still considered to be a pathological condition with a very high fatality rate that is extremely difficult to cure. Furthermore, activated protein C is an endogenous protein that activates not only coagulation-suppressing functions, but also fibrinolytic functions, thereby inhibiting thrombus formation or inflammation (DePalo et al., Advances in Sepsis 1: 114, 2001). In addition to the palliative effects of activated protein C, it is inferred that APC increases the risk of bleeding because of its features. In particular, intracranial hemorrhage is a severe adverse event. Thus, administration of APC necessitates sufficient care so that APC is administered in compliance with contraindicated conditions. Attempts that have been made other than the aforementioned attempts are as shown below.

(1) Large amounts of steroids: Application of large amounts of steroids has succeeded as a pretreatment for animals with endotoxemia or bacillaemia. Based on such successes, the effects of administration of large amounts of steroids to patients with septic shock have been examined in early clinical tests. However, in large-scale double-blind studies, validity has never been reported even in cases of administration of steroids during early development of septic shock (Meduri et al., Sepsis 3: 21, 1999; Bernard et al., N Engl J Med 317: 1565, 1987; Bone et al., Chest 92: 1032, 1987).

(2) Antiendotoxin antibody: Treatment with a specific antiendotoxin antibody has been examined using polyclonal human immunoglobulin G against heat-sterilized *E. coli* J5, mouse (E5) and humanized (HA1A) monoclonal antibodies against endotoxin lipid A, and the like. Patients with severe gram-negative bacterial infectious disease have been examined as subjects (Llewelyn et al., Sepsis 3: 39, 1999). Validity has never been confirmed in large-scale tests.

(3) Anti-TNF treatment: Anti-TNF treatment is neutralization therapy targeting TNF-α (inflammatory cytokine), which uses an anti-TNF monoclonal antibody and a soluble TNF receptor. It has been reported that survival prospects can be improved in many sepsis models via suppression of the effects of TNF-α (Tracey et al., Nature 330: 662, 1987; Pennington et al., Clin Infect Dis 17 (Suppl 2): S515, 1993). Although a plurality of phase II and phase III clinical tests have been conducted, it has never been reported that survival rates have been improved by suppressing the effects of TNF-α with the use of anti-TNF treatment (Abraham et al., JAMA 273: 934, 1995; Reinhart et al., Crit Care Med 24: 733, 1996; Severansky et al., Sepsis 3: 11, 1999; Reinhart et al., Crit Care Med 29: S121, 2001).

(4) IL-1 receptor antagonist (IL-IRa): IL-1 is also an inflammatory cytokine, but is known to induce many pathological conditions of sepsis (Ohlsson et al., Nature 348: 550 1990). Such effects can be suppressed with the use of IL-IRa, which is a natural IL-1 receptor antagonistic substance. However, a lack of differences between a treatment group (group of treated patients) and a placebo group in terms of survival rate has been demonstrated by three tests (two double-blind tests) conducted for severe sepsis patients (Fisher et al., JAMA 271: 1836, 1994; Opal et al., Crit Care Med 25: 1115, 1997; Severansky et al., Sepsis 3: 11, 1999).

(5) PAF receptor antagonist (PAFra): Platelet agglutinating factor (PAF) is a phospholipid involved in cytokine release during sepsis. It has been demonstrated by two double-blind tests that PAF receptor antagonist (BN52021) does not significantly improve survival (Dhainaut et al., Crit Care Med 22: 1720, 1994; Dhainaut et al., Crit Care Med 26: 1963, 1998; Severansky et al., Sepsis 3: 11, 1999). It has been recently demonstrated again by a phase II clinical test using another compound (BB-882) that the compound does not significantly improve the survival of severe sepsis patients.

(6) Nonsteroidal anti-inflammatory drug: an antiprostaglandin drug, Ibuprofen, has been examined in three double-blind tests, but the usefulness of Ibuprofen has never been demonstrated in any of these cases (Bernard et al., N Engl J Med 336: 912, 1997; Severansky et al., Sepsis 3: 11, 1999).

(7) Bradykinin antagonist: Bradykinin is a bioactive peptide involved in cytokine release and changes in blood vessels during sepsis. Improvement in lethality with the use of a bradykinin antagonist has never been observed in two double-blind tests (Fein et al., JAMA 277: 482, 1997; Severansky et al., Sepsis 3: 11, 1999).

As described above, although various therapeutic methods for sepsis have been advanced, suppression of the incidence rate has never been confirmed. Sepsis is still a disease for which reduction in the number of deaths therefrom has been impossible to achieve. Novel exploitation of preventive methods or therapeutic methods for sepsis are required.

RANKL, which is a ligand of RANK, is an osteoclastic differentiation-inducing factor and is known to induce osteoclasts from precursor cells of the macrophage system under coexistence with a macrophage colony-stimulating factor (M-CSF) (see Yasuda et al., Proc Natl Acad Sci USA 95: 3597, 1998 and Lacey et al., Cell 93: 165, 1998). Specifically, RANKL is produced by osteoblasts and binds to RANK on precursor cells of the macrophage system, so as to induce the cells to become osteoclasts. Furthermore, at this time, OPG (osteoprotegerin) structurally analogous to RANK suppresses the effects of RANKL, as a decoy receptor. In this manner, bone metabolism is controlled by balancing RANKL and OPG amounts. RANKL is a membrane-associated protein and a part thereof is present in blood in a soluble form. Some bone metabolism diseases confirmed with variation in the concentration of soluble RANKL (sRANKL) have been reported. The usefulness of RANKL as a bone metabolism marker has been suggested, and medical applications of RANKL have been examined (see Rogers et al., J Clin Endoceinol Metab 90: 6323, 2005 and see JP Patent Publication (Kohyo) No. 2004-526748 A; JP Patent Publication (Kohyo) No. 2002-509430 A; and International Publication WO98/46644). Moreover, discussion often takes place concerning RANKL based on the concentration ratio of soluble RANKL to OPG; that is, the ratio of the concentration of soluble RANKL to OPG. As described above, the role of RANKL in the bone metabolism system has been conventionally known; however, the functions of RANKL in the natural immune system have remained unclear and the biological meaning of soluble RANKL existing in blood has also remained unclear.

DISCLOSURE OF THE INVENTION

Objects to be Achieved by the Invention

An object of the present invention is to provide a method for prevention or treatment of symptoms resulting from inflammatory diseases such as infectious diseases, allergies, and autoimmune diseases with the use of RANKL and to provide a composition for prevention or treatment. Particularly, an object of the present invention is to prevent death due to such inflammatory diseases and to treat such diseases. Moreover, an object of the present invention is to provide a method and a reagent for measuring the concentrations of membrane-bound and soluble RANKL and the concentration of OPG, and the like existing in vivo (e.g., in blood or in synovial fluids) as markers for prediction of the degree of inflammation and risks such as the lethality of inflammatory diseases.

Means to Achieve the Objects

As described above, the roles of RANKL in bone metabolism are known. However, the functions of RANKL in the natural immune system have not been elucidated and the biological meanings of RANKL existing in blood have remained unclear.

The present inventors have considered the possible involvement of RANKL in control of the natural immune system and then examined the action of soluble RANKL on macrophages. As a result, the present inventors have discovered that inflammatory cytokine production due to infection is suppressed in various macrophages because of the effects of soluble RANKL. Furthermore, based on the fact that the concentration of blood-soluble RANKL rapidly decreases within several hours after infection, while the concentration of OPG increases, the present inventors have discovered that soluble RANKL alone, OPG alone, or a combination of soluble RANKL and OPG can be a sensitive novel marker for infection. Moreover, the present inventors have discovered that administration of soluble RANKL makes it possible to prevent septic shock due to a drug and that a soluble RANKL can be used as an agent for preventing inflammation or as an anti-inflammatory agent. Thus, the present inventors have completed the present invention.

The present invention is as follows.

[1] A method for detection of an inflammatory disease with the use of RANKL and/or OPG as a marker in a biological sample.

[2] The method for detection of an inflammatory disease according to [1], which is a method for detection of an inflammatory disease with the use of RANKL as a marker in a biological sample, comprising determining that a subject is affected with an inflammatory disease when the concentration of soluble RANKL in a biological sample is lower than that of a normal subject.

[3] The method for detection of an inflammatory disease according to [1], which is a method for detection of an inflammatory disease with the use of OPG as a marker in a biological sample, comprising determining that a subject is affected with an inflammatory disease when the concentration of OPG in a biological sample is higher than that of a normal subject.

[4] The method for detection of an inflammatory disease according to [1], which is a method for detection of an inflammatory disease with the use of RANKL and OPG as markers in a biological sample, comprising determining that a subject is affected with an inflammatory disease when the ratio of the concentration of soluble RANKL to the concentration of OPG in a biological sample is lower than that of a normal subject.

[5] The method for detection of an inflammatory disease according to [1], which is a method for detection of an inflammatory disease with the use of RANKL as a marker in a biological sample, comprising measuring membrane-type RANKL existing on a cell in a biological sample by a flow cytometric method.

[6] The method for detection of an inflammatory disease according to [1], which is a method for detection of an inflammatory disease with the use of RANKL and OPG as markers in a biological sample, comprising measuring membrane-type RANKL existing on a cell in a biological sample by a flow cytometric method and then determining that a subject is affected with an inflammatory disease when the ratio of the amount of membrane-type RANKL measured to the concentration of OPG is lower than that of a normal subject.

[7] The method for detection of an inflammatory disease according to [5] or [6], in which the cell in a biological sample is a peripheral blood cell.

[8] The method for detection of an inflammatory disease according to any one of [1] to [7], in which the inflammatory disease is an infectious disease, an allergic disease, or an autoimmune disease.

[9] The method for detection of an inflammatory disease according to [8], in which the inflammatory disease is sepsis.

[10] A detection reagent for detection of an inflammatory disease with the use of RANKL and/or OPG as a marker, comprising an anti-RANKL antibody and/or an anti-OPG antibody.

[11] A detection reagent for detection of an inflammatory disease with the use of RANKL and/or OPG as a marker, comprising an anti-RANKL antibody and an anti-OPG antibody.

[12] The detection reagent for detection of an inflammatory disease according to [10] or [11], in which the inflammatory disease is an infectious disease, an allergic disease, or an autoimmune disease.

[13] The detection reagent for detection of an inflammatory disease according to [12], in which the inflammatory disease is sepsis.

[14] A composition for prevention or treatment of an inflammatory disease, comprising RANKL and/or M-CSF as an active ingredient.

[15] The composition for prevention or treatment of an inflammatory disease according to [14], comprising RANKL and M-CSF as active ingredients.

[16] The composition for prevention or treatment of an inflammatory disease according to [15], in which the composition for prevention or treatment of an inflammatory disease is a combination preparation.

[17] The composition for prevention or treatment of an inflammatory disease according to [15], in which the composition is a kit comprising a drug that contains RANKL and a drug that contains M-CSF.

[18] The composition for prevention or treatment of an inflammatory disease according to any one of [15] to [17], which is characterized in that RANKL and/or M-CSF is administered before surgery, so as to prevent a postoperative inflammatory disease.

[19] The composition for prevention or treatment of an inflammatory disease according to any one of [15] to [18], in which the inflammatory disease is an infectious disease, an allergic disease, or an autoimmune disease.

[20] The composition for prevention or treatment of an inflammatory disease according to [19], in which the inflammatory disease is sepsis.
[21] An immunosuppressive agent, comprising RANKL and/or M-CSF as an active ingredient.
[22] The immunosuppressive agent according to [21], comprising RANKL and M-CSF as active ingredients.
[23] The immunosuppressive agent according to [22], in which the immunosuppressive agent is a combination preparation.
[24] The immunosuppressive agent according to [23], in which the immunosuppressive agent is a kit comprising a drug that contains RANKL and a drug that contains M-CSF.

Effects of the Invention

When a subject is affected with an inflammatory disease such as an infectious disease, RANKL expression decreases and OPG expression increases. Therefore, an inflammatory disease can be detected and diagnosed by measurement of the amount of RANKL or OPG. Particularly when the ratio of the amount of RANKL to the amount of OPG is used as an indicator, high-precision detection and diagnosis can be performed.

Furthermore, RANKL and/or M-CSF has an effect of suppressing inflammatory cytokine production by various macrophages. Moreover, an inflammatory disease can be prevented or treated with the use of RANKL and/or M-CSF.

BRIEF DESCRIPTION OF THE DRAWINGS

FIG. 9 shows changes in serum soluble RANKL and OPG concentrations in response to LPS injection.

FIG. 10 shows changes in serum soluble RANKL and OPG concentrations in response to *Salmonella* infection.

FIG. 11 shows serum soluble RANKL and OPG concentrations in wild-type mice and mice lacking RANKL (Tnfsf11$^{-/-}$).

FIG. 13 shows serum soluble RANKL and OPG concentrations in wild-type mice and mice lacking OPG (Tnfrsf11b$^{-/-}$).

FIG. 19 shows the nucleotide sequence of cDNA that encodes human-type RANKL residues 140 to 317 (SEQ ID No: 14) and the corresponding amino acid sequence (SEQ ID No: 10).

FIG. 21A shows the nucleotide sequence of a vector containing a RANKL gene (1/2, continuing to FIG. 21B) (SEQ ID No: 11).

FIG. 21B shows the nucleotide sequence of a vector containing the RANKL gene (2/2, continued from FIG. 21A) (SEQ ID No: 11).

BEST MODE OF CARRYING OUT THE INVENTION

Figure 1:
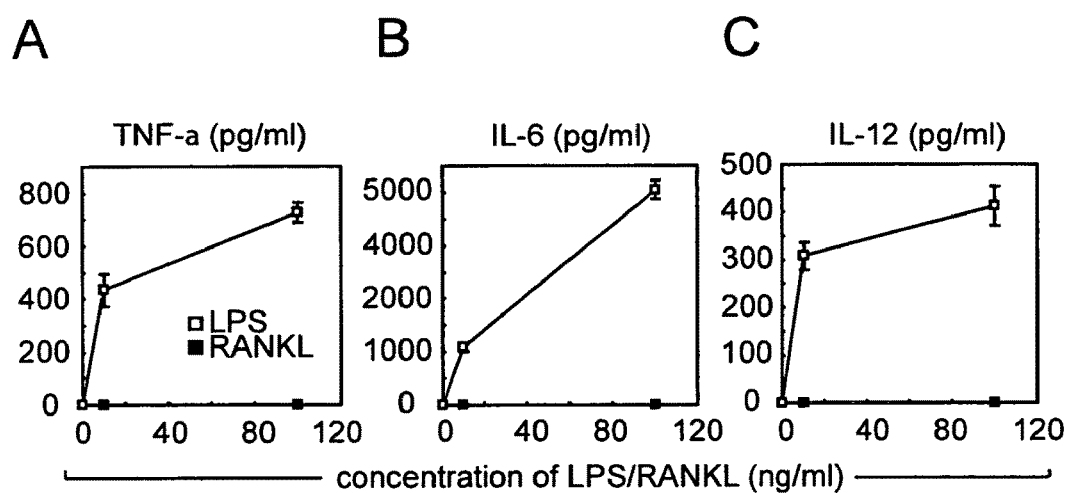
FIG. 1 shows a lack of the induction of cytokine production due to soluble RANKL.

RANKL (Receptor activator of NF-κB ligand) is a ligand of RANK (receptor activator of NF-κB) that is a member of the TNF superfamily and is a type II transmembrane protein having an intracellular domain (the domain comprising amino acids 1 to 48 from the N terminus of RANK), a transmembrane domain, and an extracellular domain (JP Patent Publication (Kohyo) No. 2002-509430 and International Publication WO98/46644 pamphlet). In the extracellular domain, a domain comprising amino acid 152 (from the N terminus) and the following amino acids is a TNF ligand family homologous domain.

OPG (osteoprotegerin) has a structure analogous to that of RANK and can bind to RANKL.

When a subject is affected with an inflammatory disease, RANKL expression decreases, OPG expression increases, blood soluble RANKL concentration decreases, and OPG concentration increases.

The method of the present invention is a method for detection of an inflammatory disease, which comprises measuring RANKL and/or OPG in a biological sample collected from a subject and performing detection with the use of RANKL and/or OPG as a marker. RANKL to be measured in the method of the present invention is soluble RANKL (sRANKL) secreted in a biological sample that is a body fluid such as blood or membrane-type RANKL existing on cells in peripheral blood or the like.

Examples of a biological sample include blood, plasma, serum, tears, urine, amniotic fluids, synovial fluids, spinal fluids, cell extracts, tissue extracts, cells, and tissues. The effects of an inflammatory disease are often expressed throughout the body, so that blood, plasma, and serum are preferable among the above biological samples.

In the method of the present invention, the term "inflammatory disease" refers to a generic term of diseases with the presentation of inflammatory symptoms, including infectious diseases, allergy diseases, and autoimmune diseases, for example. Examples of such diseases include severely diseased trauma, burn, surgical invasion, acute pancreatitis, peritonitis, malignant tumor, acute abdomen (abdominal disease with an acute abdominal pain as a predominant symptom, which requires emergency surgery), infectious diseases (particularly, nosocomial infections due to Gram-negative bacteria such as *Serratia, Pseudomonas aeruginosa, Acinetobacter, Citrobacter*, and *Enterobacter*), and a severe acute disease (namely, SIRS) requiring treatment in ICU, such as sepsis. Furthermore, allergy diseases such as contact hypersensitivity, allergic rhinitis, food allergy, and asthma are also diseases to be subjected to the method of the present invention. Further examples of the inflammatory disease include inflammatory skin diseases such as atopic dermatitis, contact dermatitis, photosensitive dermatitis, chronic dermatitis of fingers and toes, seborrheic dermatitis, nummular dermatitis, generalized exfoliative dermatitis, stasis dermatitis, local dermatitis due to abrasion, dermatitis medicamentosa, or psoriasis. Further examples of the inflammatory disease include autoimmune diseases such as rheumatoid arthritis, scleroderma, dermatomyositis, autoimmune vasculitis, mixed connective tissue disease, systemic erythematosus, idiopathic thrombocytopenic purpura, Crohn's disease, and human adjuvant disease.

Whether or not a subject is affected with the above inflammatory disease can be detected and diagnosed by the method of the present invention. Furthermore, the severity of the above inflammatory disease can be evaluated and determined. In particular, the severity of sepsis can be evaluated and determined.

A method for measuring RANKL and/or OPG is not limited. For example, RANKL and/or OPG can be measured by immunoassay using an anti-RANKL antibody and/or an anti-OPG antibody, such as Western blotting, EIA, RIA, an agglutination method, immunochromatography, or a flow cytometric method. When membrane-bound RANKL on cells in peripheral blood or the like is measured, a bound RANKL level (amount of RANKL) on cells is measured by a flow cytometric method. Measurement by flow cytometry can be performed using a flow cytometer such as a commercially available FACS. An anti-RANKL antibody and/or anti-OPG antibody can be prepared by a known method. When measurement is performed using an antibody, an antibody to be used herein is labeled adequately with an enzyme such as alkaline phosphatase or a fluorescent dye. In addition, extracellular domains of soluble RANKL and membrane-type RANKL are subjected to measurement in the present invention, an anti-RANKL antibody preferred herein recognizes and binds to the extracellular domains of soluble RANKL and membrane-type RANKL. Soluble RANKL contains no intracellular domain, so that an anti-RANKL antibody to be used in the method of the present invention is an antibody capable of recognizing an extracellular domain other than the intracellular domains of RANKL and preferably recognizing an epitope that exists in a TNF ligand family homologous domain. Furthermore, a commercially available antibody can also be used. Furthermore, RANKL and/or OPG mRNA is detected and then the expression of RANKL and/or OPG may be detected. mRNA can be detected by Northern blotting, an RT-PCR method, a method using DNA chips (DNA microarray), or the like. At this time, a probe or primers comprising partial sequences complementary to the partial sequences of mRNA encoding RANKL and/or OPG are used for measuring specifically mRNA that encodes RANKL and/or OPG. The nucleotide sequences of RANKL and OPG are known.

Probes or primers can be designed based on the known nucleotide sequence information. The number of the nucleotides of a primer or a probe ranges from 5 to 50, preferably 10 to 30, and further preferably 15 to 25. These methods can be performed by known methods.

When a RANKL concentration or amount in a sample collected from a subject is significantly lower than that of a normal subject or when an OPG concentration is significantly higher than that of a normal subject, the subject can be diagnosed as being affected with an inflammatory disease. Furthermore, it can be evaluated and determined that the lower the RANKL concentration or amount or the higher the OPG concentration, the severer the inflammatory disease such as sepsis.

Moreover, when the concentration ratio of soluble RANKL to OPG (soluble RANKL concentration: OPG concentration) in a sample collected from a subject is lower than that of a normal subject, the subject can be diagnosed as being affected with an inflammatory disease. Furthermore, it can be evaluated and determined that the lower the concentration ratio of soluble RANKL to OPG, the severer the inflammatory disease such as sepsis.

The expression of RANKL and/or OPG can fluctuate within several hours after the onset of an inflammatory disease. Hence, an inflammatory disease can be detected at an early phase according to the method of the present invention. Furthermore, several times of measurement of RANKL and/or OPG at appropriate time intervals enables more precise detection.

The present invention encompasses a reagent or a kit for detection of an inflammatory disease with the use of RANKL and/or OPG as a marker. The reagent or the kit comprises an anti-RANKL antibody and/or an anti-OPG antibody. When soluble RANKL and OPG are measured by ELISA or the like, an antibody may be labeled with an enzyme such as alkaline phosphatase or horseradish peroxidase. In addition, when membrane-bound RANKL is measured by a flow cytometric method, an antibody against RANKL may be labeled with a fluorescent dye.

The present invention further encompasses a marker for detection of an inflammatory disease, which comprises RANKL and/or OPG. The present invention further encompasses the use of RANKL and/or OPG as a marker for detection of an inflammatory disease.

The present invention further encompasses a composition (anti-inflammatory agent) or an immunosuppressive agent for treatment or prevention of an inflammatory disease, comprising RANKL and/or M-CSF as an active ingredient. When RANKL alone or a combination of RANKL and M-CSF is administered to a subject, inflammatory cytokine production by macrophages is suppressed in the subject, TLR4 level is suppressed, and the antigen-presenting ability of antigen-presenting cells of the subject is suppressed. Accordingly, RANKL and M-CSF can be used independently or in combination for treatment or prevention of inflammatory diseases. Furthermore, the immunity of a subject can be suppressed by the use of RANKL and M-CSF independently or in combination. In addition, RANKL-induced tolerance (RANKL tolerance) in macrophages is independent from c-Fos required for osteoclast differentiation. Thus, the effects of RANKL on macrophages differ from the "phenomenon of differentiation from macrophages" in the process of differentiation of macrophages into osteoclasts.

The term "inflammatory disease" which is a target of the composition for prevention or treatment of the present invention is a generic term for diseases with presentation of inflammatory symptoms, including infectious diseases, allergy diseases, and autoimmune diseases, for example. Examples of such diseases include severely diseased trauma, burn, surgical invasion, acute pancreatitis, peritonitis, malignant tumor, acute abdomen (abdominal disease with an acute abdominal pain as a predominant symptom, which requires emergency surgery), infectious diseases (particularly, nosocomial infections due to Gram-negative bacteria), and a severe acute disease (namely, SIRS) requiring treatment in ICU, such as sepsis. Furthermore, allergy diseases such as contact hypersensitivity, allergic rhinitis, food allergy, and asthma are also diseases to be subjected to the method of the present invention. Further examples of the inflammatory disease include inflammatory skin diseases such as atopic dermatitis, contact dermatitis, photosensitive dermatitis, chronic dermatitis of fingers and toes, seborrheic dermatitis, nummular dermatitis, generalized exfoliative dermatitis, stasis dermatitis, local dermatitis due to abrasion, dermatitis medicamentosa, or psoriasis. Further examples of the inflammatory disease include autoimmune diseases such as rheumatoid arthritis, scleroderma, dermatomyositis, autoimmune vasculitis, mixed connective tissue disease, systemic erythematosus, idiopathic thrombocytopenic purpura, Crohn's disease, and human adjuvant disease.

Examples of RANKL that can be used for the composition for treatment or the immunosuppressive agent of the present invention include RANKL, soluble RANKL, a soluble RANKL derivative, a soluble RANKL analog, a soluble RANKL fusion protein, or a soluble RANKL mimic. The full-length nucleotide sequence and amino acid sequence of human-derived RANKL are shown in SEQ ID NO: 1 and 2, respectively. A soluble RANKL derivative or a soluble RANKL analog is a protein comprising a partial sequence of the amino acid sequence of RANKL, such as truncated RANKL. A protein having RANKL activity is also included herein. A soluble RANKL derivative preferably contains a TNF ligand family homologous domain that begins from amino acid 152 in the amino acid sequence of SEQ ID NO: 2. Examples of such a soluble RANKL derivative include a protein comprising the amino acid sequence ranging from amino acid 127 to amino acid 317, a protein comprising the amino acid sequence ranging from amino acid 140 to amino acid 317, or a protein comprising the amino acid sequence ranging from amino acid 159 to amino acid 317. Furthermore, examples of a soluble RANKL derivative or a soluble RANKL analog include a protein comprising an amino acid sequence that comprises a deletion, substitution, or addition of one or several amino acids with respect to the amino acid sequence represented by SEQ ID NO: 2 and having RANKL activity, and a protein comprising an amino acid sequence that comprises a deletion, substitution, or addition of one or several amino acids with respect to the amino acid sequence of a protein that comprises a partial sequence of the amino acid sequence of the above RANKL and having RANKL activity. Here, the term "one or several" refers to 1 to 9, preferably 1 to 5, and further preferably 1 or 2. The term "soluble RANKL fusion protein" refers to a fusion protein prepared by fusing another protein to a soluble RANKL protein, a soluble RANKL derivative, or a soluble RANKL analog. An example of such "another protein" is glutathione S-transferase (GST). The nucleotide sequence of DNA encoding a fusion protein prepared by fusing GST to a protein comprising an amino acid sequence ranging from amino acid 127 to amino acid 317 in the amino acid sequence of RANKL and the amino acid sequence of the fusion protein are shown in SEQ ID NOS: 3 and 4, respectively. The nucleotide sequence of DNA encoding a fusion protein prepared by fusing GST to a protein comprising an amino acid sequence ranging from amino acid 140 to amino acid 317 in the amino acid sequence of RANKL and the amino acid sequence of the fusion protein are shown in SEQ ID NOS: 5 and 6, respectively. Furthermore, the nucleotide sequence of DNA encoding a fusion protein prepared by fusing GST to a protein comprising an amino acid sequence ranging from amino acid 159 to amino acid 317 in the amino acid sequence of RANKL and the amino acid sequence of the fusion protein are shown in SEQ ID NOS: 7 and 8, respectively. The soluble RANKL mimic is a compound having a structure analogous to the conformation of RANKL and having RANKL activity. Such RANKL, soluble RANKL, soluble RANKL derivative, soluble RANKL analog, and soluble RANKL fusion protein can be prepared as recombinant proteins by gene-engineering techniques.

Examples of M-CSF to be used for the composition for prevention or treatment or the immunosuppressive agent of the present invention include, similarly to examples of RANKL, M-CSF, an M-CSF derivative, an M-CSF analog, an M-CSF fusion protein, and an M-CSF mimic. Such M-CSF, M-CSF derivative, M-CSF analog, and M-CSF fusion protein can be prepared as recombinant proteins by gene-engineering techniques. Furthermore, a commercially available M-CSF preparation can also be used. An example of such M-CSF is Leukoprol (Trademark, general name: mirimostim).

RANKL alone may be administered to a subject or M-CSF alone may also be administered to a subject for prevention or treatment of an inflammatory disease or immunosuppression. Preferably, both RANKL and M-CSF are administered. When both RANKL and M-CSF are administered, the mixture of the two, that is, a combination preparation prepared by mixing the two can be administered simultaneously. Furthermore, a composition containing RANKL and a composition containing M-CSF are separately formulated, and then the two preparations can be mixed when used and then administered. Furthermore, the preparations may be administered separately in turn. Preferably, both RANKL and M-CSF are administered simultaneously. The composition for prevention or treatment or the immunosuppressive agent of the present invention is also a kit comprising a drug containing RANKL and a drug containing M-CSF for administration of RANKL and M-CSF separately.

Moreover, when the composition for prevention or treatment of an inflammatory disease of the present invention is used for treatment, the composition is administered to a patient affected with an inflammatory disease. Furthermore, when the composition is used for prevention, the composition is administered to a patient suspected of being affected with an inflammatory disease. For example, the composition is administered to a patient affected with a severe infectious disease who may be suspected of developing sepsis or SIRS. Furthermore, for prevention of postoperative infection, the composition of the present invention may be administered before invasive surgery. The immunosuppressive agent of the present invention comprising RANKL and/or M-CSF as an active ingredient is administered to a patient when a tissue or an organ is transplanted in the patient. The immunosuppressive agent of the present invention can suppress graft rejection associated with cell or organ and/or tissue transplantation and graft-versus-host disease.

The composition for prevention or treatment of an inflammatory disease or the immunosuppressive agent of the present invention can be administered in various forms. For example, the composition can be orally administered in the form of tablets, capsules, fine granules, powders, syrups, or the like or can also be parenterally administered in the form of injections, drops, suppositories, sprays, eye drops, intranasal agents, and adhesive preparations, or the like.

The composition for prevention or treatment of an inflammatory disease or the immunosuppressive agent of the present invention contains a carrier, a diluent, and an excipient, which are generally used in the pharmaceutical field. For example, as a carrier and an excipient for tablets, lactose, magnesium stearate, and the like are used. As an aqueous solution for injection, a physiological saline solution, an isotonic solution containing glucose or other adjunctive agents, or the like is used. These examples may also be used in combination with an appropriate solubilizing agent such as alcohol, polyalcohol such as propylene glycol, a nonionic surfactant, and the like. As an oily liquid, sesame oil, soybean oil, or the like is used. As a solubilizing agent, benzyl benzoate, benzylalcohol, or the like may also be used in combination.

The dose is varied depending on symptoms, age, body weights, and the like. The dose in the case of oral administration ranges from approximately 0.001 mg to 1000 mg per day, and administration may be performed once or in divided doses. Furthermore, the dose in the case of parenteral administration ranges from 0.001 mg to 1000 mg per administration, and administration is performed by intravenous injection, intraperitoneal injection, subcutaneous injection, or intramuscular injection or using a suppository, an eye drop, or the like. When RANKL and M-CSF are used in combination, the ratio of the dose of RANKL to the dose of M-CSF is not limited. RANKL and M-CSF may be administered in the same amounts, or the amount of either soluble RANKL or M-CSF to be administered may be greater than the other.

The present invention further encompasses a method for prevention or treatment of an infectious disease or an immunosuppression method, comprising administering soluble RANKL and/or M-CSF to a patient who needs prevention or treatment.

The present invention further encompasses the use of soluble RANKL and/or M-CSF for production of a composition for prevention or treatment of an infectious disease or the use of the same for production of an immunosuppressive agent.

The present invention further encompasses soluble RANKL and/or M-CSF to be used for treatment of an infectious disease or soluble RANKL and/or M-CSF to be used for immunosuppression.

EXAMPLES

The present invention is hereafter described in greater detail with reference to the following examples, although the present invention is not limited thereto.

The following materials and methods are used in the Examples.

Mice

Six to 10-week-old C57BL/6J mice were purchased from Oriental Yeast Co., Ltd. Homozygous mice lacking OPG and control heterozygous mice with a C57BL/6J background were purchased from Clea Japan. Mice lacking RANKL and mice lacking TLR4 with a C57BL/6J background were bred and maintained under specific pathogen-free conditions (SPF). A powder diet was provided to mice lacking RANKL. All experiments were performed in accordance with guidelines for animal use at the Keio University School of Medicine or Oriental Yeast Co., Ltd.

M-CSF-dependent Macrophage

To generate M-CSF-dependent bone marrow-derived macrophages (MDBMs), bone marrow cells were harvested by flushing tibias and femurs with Dulbeco's modified Eagle's medium (DMEM) containing 10% fetal calf serum (FCS) and antibiotics. After passage through a cell strainer, bone marrow cells were cultured overnight. Non-adherent cells were harvested and cultured in the presence of 10 ng/ml M-CSF. After 3 to 4 days, cells that had adhered to the wells were harvested using a cell scraper and then seeded as M-CSF-dependent bone marrow-derived macrophages at a concentration of $1\times10^5$/well in a 24-well plate (Falcon). M-CSF-dependent spleen-derived macrophages (MDSMs) were generated from splenocytes by a method similar to the above method. All macrophages were cultured in the presence of 10 ng/ml M-CSF in all experiments.

Peritoneal Macrophages

Peritoneal cells were harvested by flushing the peritoneal cavity of mice with complete medium (DMEM containing 10% FCS and antibiotics). The thus harvested cells were seeded at a concentration of $1\times10^5$/well in a 24-well plate (Falcon). Cells were cultured for 6 hours, the plate was washed with PBS to remove non-adherent cells, and remaining cells were incubated in fresh medium. The thus obtained adherent cells were used as peritoneal macrophages.

In vitro Tolerance Experiments

Macrophages were pretreated with different concentrations of soluble RANKL (<0.10 endotoxin units/mg, R&D) or LPS (also referred to as lipopolysaccharide or endotoxin; LPS used in the Examples is S. Minnesota Re595, Sigma) for given periods of time. Cultured cells were subsequently washed twice with phosphate buffered saline (PBS) and stimulated with LPS, flagellin derived from *Salmonella munchen* (Calbiochem), CpG oligonucleotide (5'-TCCATgACgTTCCTgATgCT-3'; SEQ ID NO: 12), or control GpC oligonucleotides (5'-TCCATgAgCTTCCTgATgCT-3', Proligo; SEQ ID NO: 13) as indicated in the description. In some experiments, 500 U/ml GM-CSF (Pepro Tec) was added 3 hours before stimulation of cells with LPS.

Mouse LPS Administration

Figure 23:
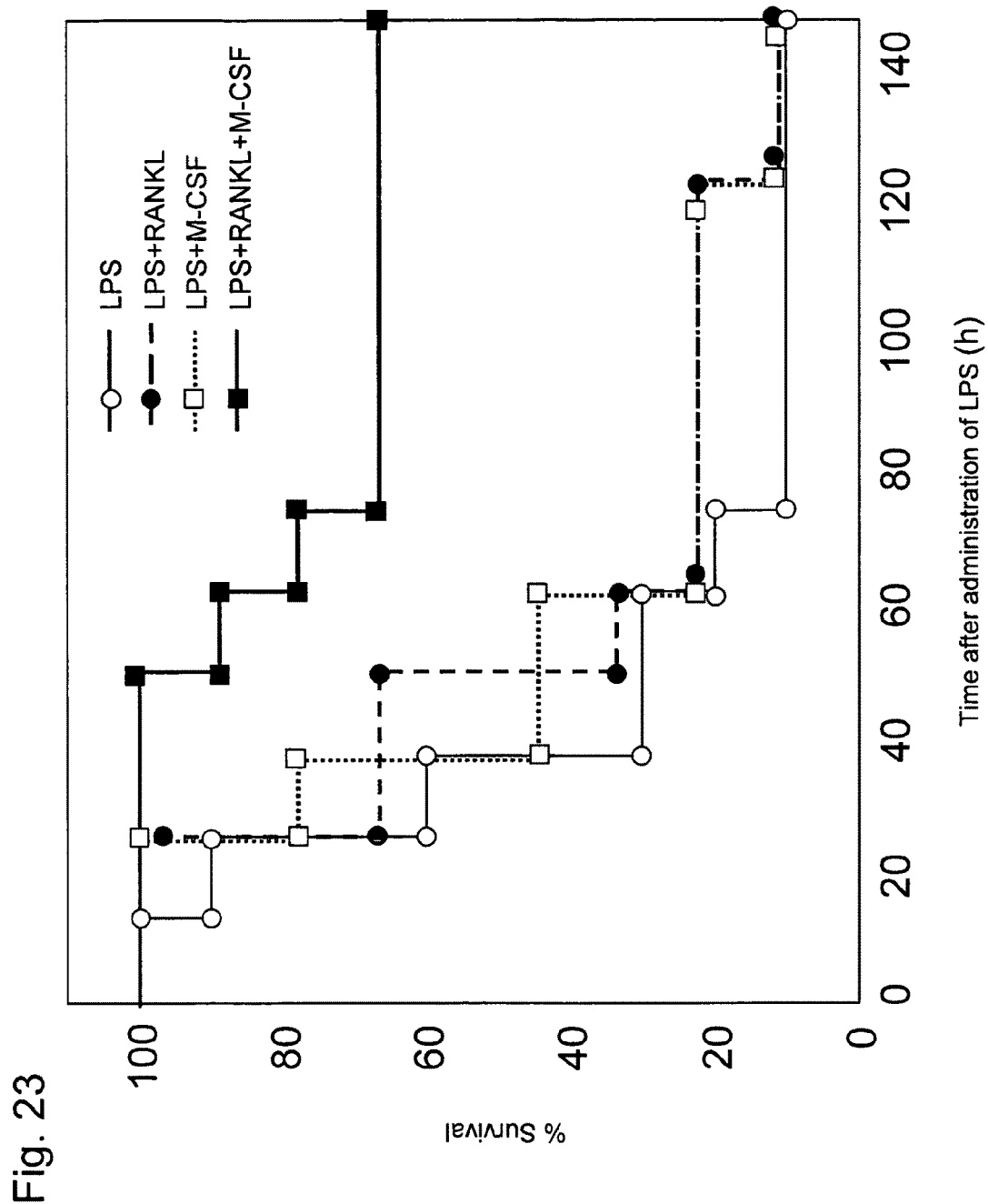
FIG. 23 shows survival percentage when LPS was administered to the mice to which GST-RANKL and/or M-CSF had been administered.

LPS (S. Minnesota Re595, Sigma) was administered intraperitoneally. LPS (*E. coli* 055: B5, Sigma) was used in the Example as shown in FIG. 23. Blood was collected by heart puncture at given time points. Blood was allowed to clot for 1 hour and then centrifuged at 15000 rpm at 24° C. for 20 minutes. The serum was stored at −80° C. until cytokine assays.

Bacterial Strain and Infection Experiment

For an infection experiment, an overnight standing culture of *Salmonella enterica* serovar Typhimurium χ 3306 strain (hereinafter, *Salmonella*) in Luria-Bartani broth (LB medium) was diluted and shaken, and mid-log phase bacteria were then collected by centrifugation. *Salmonella* was washed with PBS, diluted with Hanks' salt solution, and used to infect macrophages at a multiplicity of infection (MOI) of 10. After incubation at 37° C. for 1 hour, macrophages were washed with PBS to remove extracellular *Salmonella* and then incubated in complete medium containing 25 μg/ml gentamycin. After 3 hours, culture supernatants were harvested for cytokine assays. For oral infection with *Salmonella*, mice were subjected to fasting with no water and feed for 12 hours before infection, and then $3.3\times10^7$ CFU/g body weight of *Salmonella* was administered orally. Four days later, blood was collected by heart puncture.

Enzyme-linked Immunosorbent Assay (ELISA)

TNF-α, IL-6, and IL-12 (p40) concentrations in macrophage culture supernatants were measured using ELISA sets (BD PharMingen). Soluble RANKL and OPG concentrations in mouse serum were measured using ELISA kits (R&D).

PT-PCR Analysis mRNA was prepared by collecting macrophages and homogenizing the macrophages in Isogen (Nippon gene).

cDNA was synthesized using the Enhanced Avian HS RT-PCR kit (Sigma-Aldrich). Quantitative PCR was performed using an ABI PRISM 7000 apparatus TaqMan Assay-on-demand (Applied Biosystems) and IL-6, TNF-α, IL-12 (p40), and Gapdh primers.

Statistical Analysis

Data are expressed as means±SD (standard deviation). All data excluding those of the Example, the results of which are shown in FIG. 23, were analyzed by significant difference tests using the Student's t-test. Only in the Example, the results of which are shown in FIG. 23, significant difference tests were performed using a generalized Wilcoxon test.

The following results were obtained.

(1) Induction of RANKL Tolerance in Macrophages Stimulated with Bacterial Components First, M-CSF-dependent bone marrow-derived macrophages (MDBMs) were stimulated with soluble RANKL or LPS and then inflammatory cytokine production was measured (FIG. 1A to C). FIG. 1A to C show the lack of the induction of cytokine production because of soluble RANKL. MDBMs were stimulated with LPS or soluble RANKL with a concentration shown in FIG. 1 for 24 hours. Protein concentrations of inflammatory cytokines in culture supernatants were measured by ELISA. Bars in FIG. 1 represent means±SD (n=3, culture well). As shown in FIG. 1A to C, it was revealed that while LPS significantly induced the production of cytokines such as TNF-α, IL-6, and IL-12 (p40), soluble RANKL with a concentration as high as 100 ng/ml did not induce detectable levels of cytokine production. Therefore, unlike LPS, soluble RANKL cannot induce inflammatory cytokines.

Figure 2:
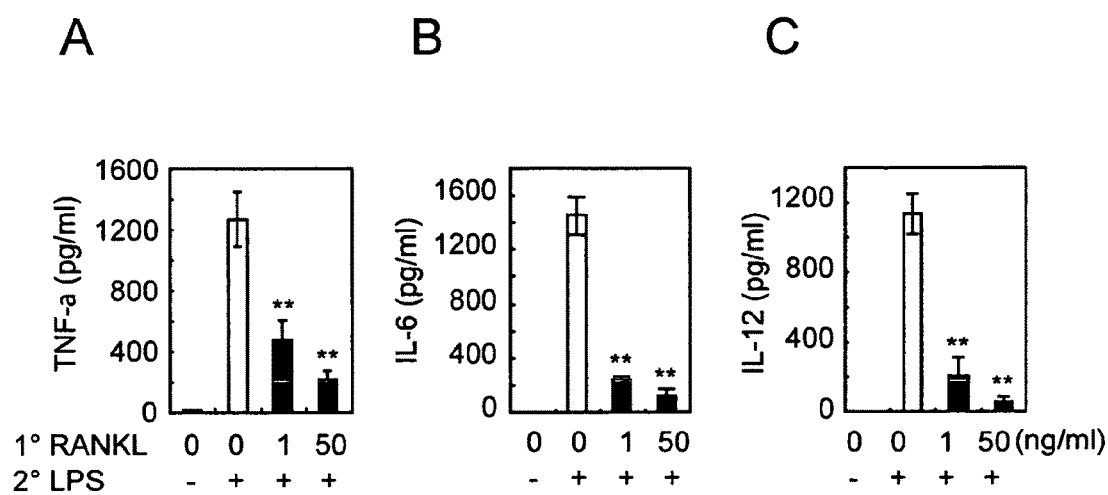
FIG. 2 shows RANKL-induced tolerance in macrophages based on inflammatory cytokine concentrations.

Next, MDBMs were pretreated for 24 hours with soluble RANKL by increasing the concentration of soluble RANKL in steps and then stimulated with LPS for 6 hours. The concentrations of TNF-α, IL-6, and IL-12 (p40) in the supernatants were measured by ELISA. As a result, it was revealed that pretreatment of soluble RANKL suppresses cytokine production resulting from subsequent stimulation with LPS in a soluble RANKL concentration-dependent manner (FIG. 2A to C). FIG. 2A to C show the protein concentration of each inflammatory cytokine, showing that RANKL-induced tolerance was induced in macrophages. MDBMs were pretreated with soluble RANKL for 24 hours (1°) and then stimulated with 100 ng/ml LPS for 6 hours (2°). As shown in FIG. 2A to C, such induced tolerance was also observed at a low concentration (as low as 1 ng/ml) of soluble RANKL.

Figure 3:
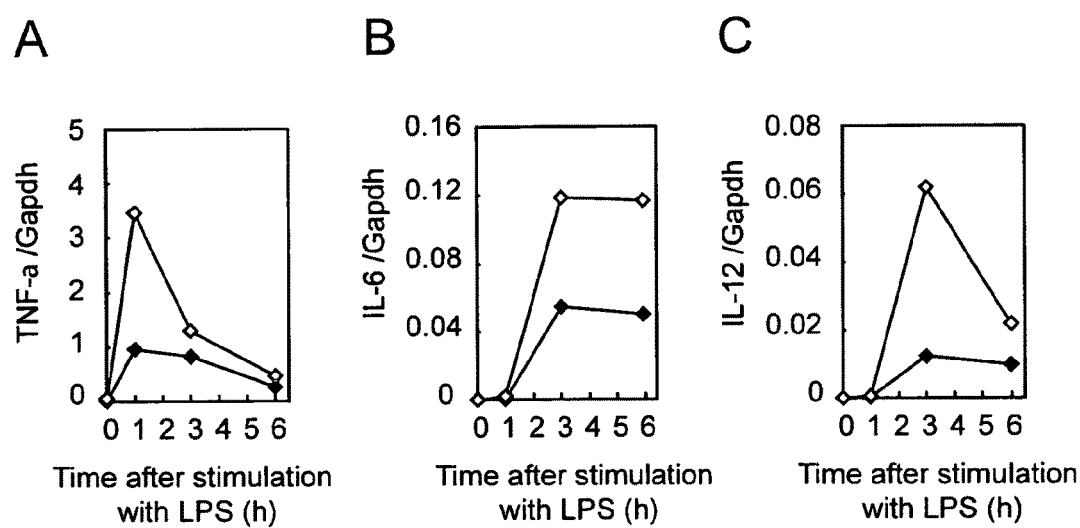
FIG. 3 shows RANKL-induced tolerance in macrophages based on inflammatory cytokine mRNA levels.

The mRNA levels of TNF-α, IL-6, and IL-12 (p40) were measured with time over 6 hours after stimulation with LPS. Compared with macrophages not pretreated with soluble RANKL, macrophages pretreated with soluble RANKL showed significantly suppressed induction of cytokine mRNAs upon LPS stimulation (FIG. 3A to C). FIG. 3A to C show the mRNA level of each inflammatory cytokine, showing that RANKL-induced tolerance was induced in macrophages. MDBMs were pretreated with medium alone (open diamonds) or 10 ng/ml soluble RANKL (close diamonds) for 24 hours and then stimulated with 100 ng/ml LPS for 6 hours. Cells were harvested at each time point as in FIG. 3. Cytokine mRNA levels were measured by quantitative PCR. Values are normalized to Gapdh.

Figure 4:
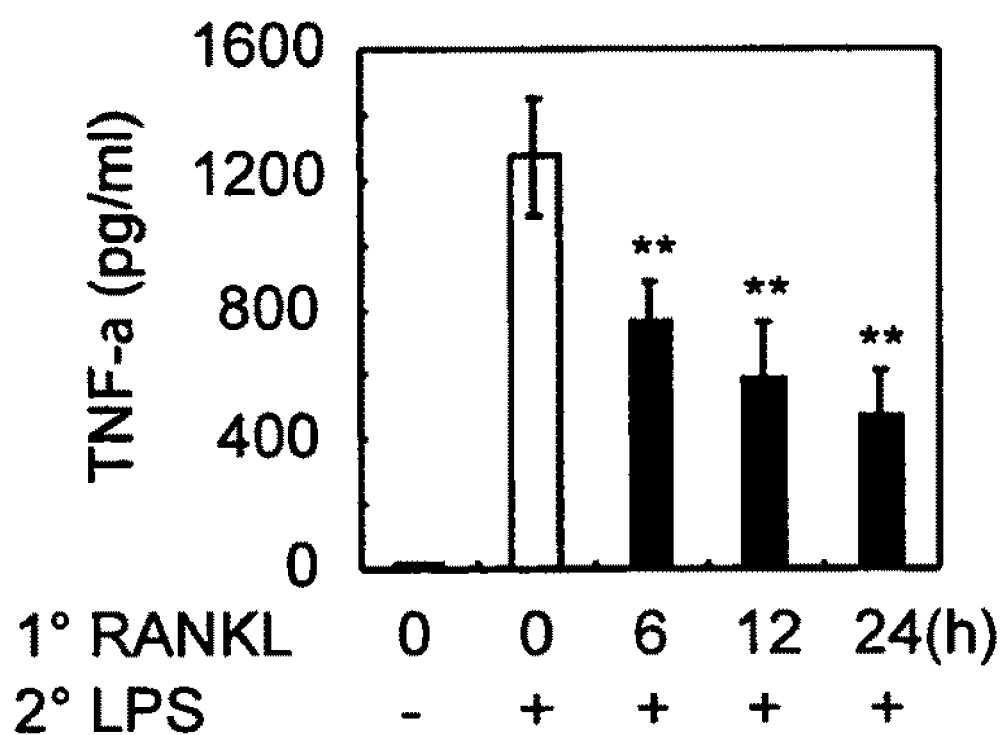
FIG. 4 shows RANKL-induced tolerance in macrophages based on the concentrations of TNF-α produced when macrophages were pretreated with soluble RANKL for given periods of time and then stimulated with LPS.

Next, the duration of pretreatment with soluble RANKL was shortened to 24 hours, 12 hours, and 6 hours. MDBMs were pretreated with 1 ng/ml soluble RANKL for given periods of time as in FIG. 4 (1°) and then stimulated with LPS (2°). As a result, it was revealed that even as short as 6 hours of pretreatment significantly suppressed the induction of TNF-α production in response to stimulation with LPS (FIG. 4).

Figure 5:
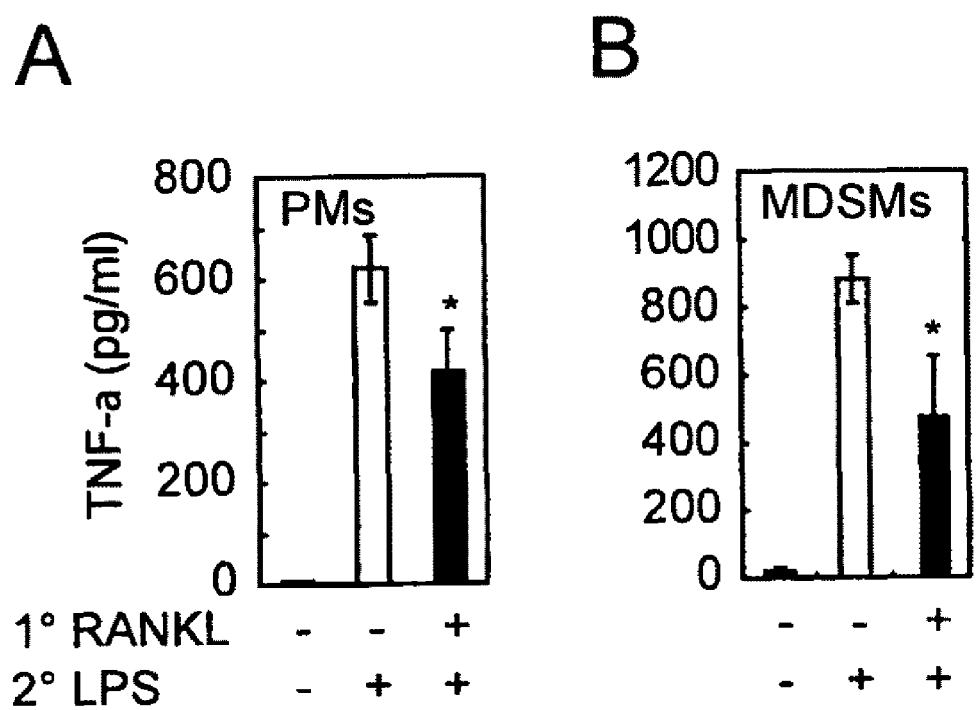
FIG. 5 shows RANKL-induced tolerance in macrophages based on the concentrations of TNF-α produced when peritoneal macrophages (PMs) and M-CSF-dependent spleen-derived macrophages (MDSMs) were pretreated with soluble RANKL for given periods of time and then stimulated with LPS.

To examine whether or not RANKL-induced tolerance takes place in macrophages other than MDBMs, an experiment was then conducted using peritoneal macrophages (PMs) and M-CSF-dependent spleen-derived macrophages (MDSMs). Peritoneal macrophages (PMs) and M-CSF-dependent spleen-derived macrophages (MDSMs) were pretreated with 50 ng/ml soluble RANKL for 24 hours (1°) and then stimulated with LPS (2°). As a result, the induction of TNF-α production in response to stimulation with LPS was suppressed in these macrophages when the macrophages had been pretreated with soluble RANKL (FIG. 5).

Figure 6:
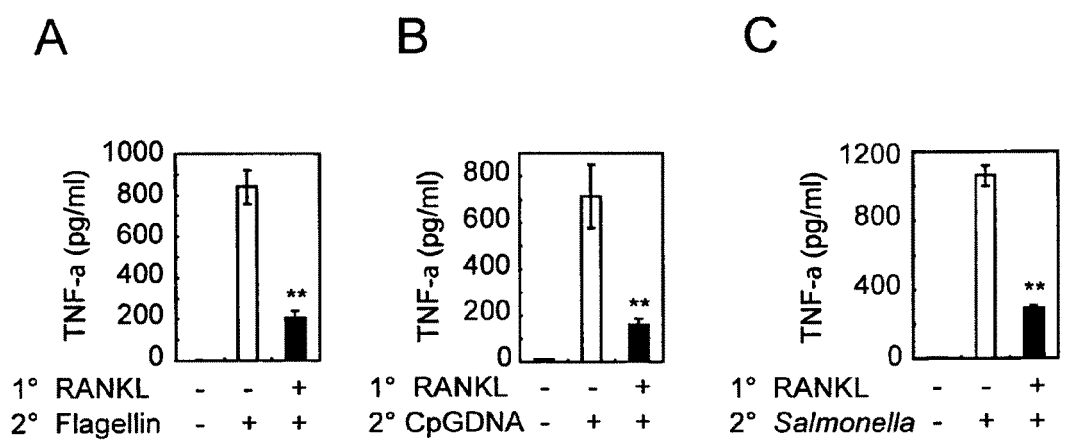
FIG. 6 shows RANKL-induced tolerance with respect to various stimulations.

Finally, MDBMs were pretreated with soluble RANKL for 24 hours and then stimulated with flagellin, CpG oligonucleotide, and *Salmonella*. MDBMs were pretreated with 10 ng/ml soluble RANKL for 24 hours (1°) and then stimulated with $1 \times 10^{-11}$ M flagellin or 3 nM CpG DNA for 6 hours or with *Salmonella* for 3 hours (2°). Cytokines in the culture supernatants were measured by ELISA. As a result, it was revealed that pretreatment with soluble RANKL suppressed the induction of TNF-α production in response to stimulation with the bacterial components or *Salmonella* (FIG. 6A to C). Bars in FIG. 6 represent means±SD (n=3, culture well). "*, P<0.05; **, P<0.01" represent the results compared with open bars. These results suggest that soluble RANKL lowers the responsiveness of macrophages to LPS or other bacterial components.

Figure 7:
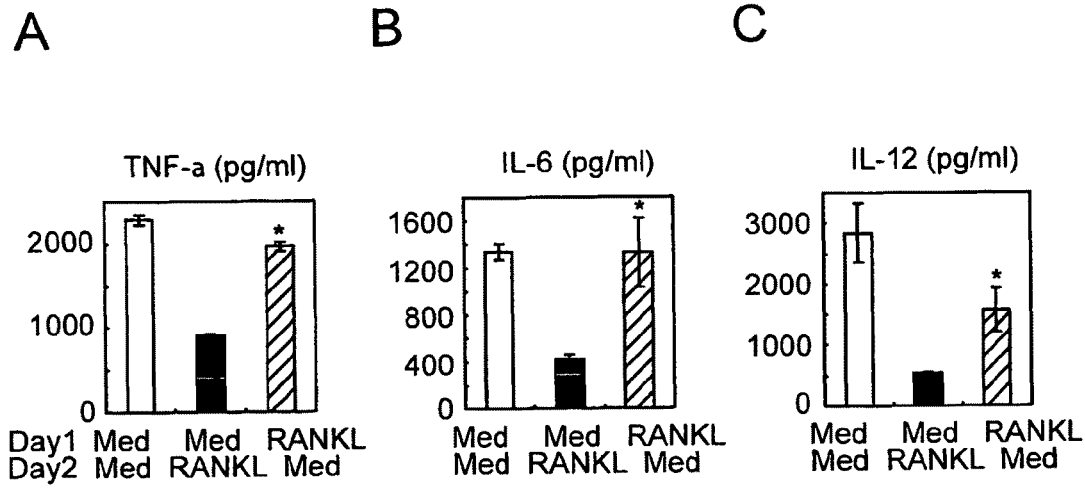
FIG. 7 shows the reversibility of RANKL-induced tolerance.

(2) Attenuation of RANKL-induced Tolerance by Soluble RANKL Removal or GM-CSF Treatment To examine whether or not RANKL-induced tolerance is reversible, MDBMs were treated with soluble RANKL for 24 hours and then cultured in soluble-RANKL-free medium for another 24 hours. MDBMs were treated with medium alone (Med) or 10 ng/ml soluble RANKL for 24 hours (Day 1), treated with medium alone (Med) or 10 ng/ml soluble RANKL for another 24 hours (Day 2), and then stimulated with 100 ng/ml LPS for 6 hours. Culture supernatants (n=3) were harvested for measurement of cytokine concentrations by ELISA. Compared with a control group, production of TNF-α, IL-6, and IL-12 (p40) was sufficiently or at least partially restored, demonstrating that RANKL-induced tolerance is reversible (FIG. 7A to C). Bars in FIG. 7 represent means±SD. "*, P<0.01" represent the results compared with close bars.

Figure 8:
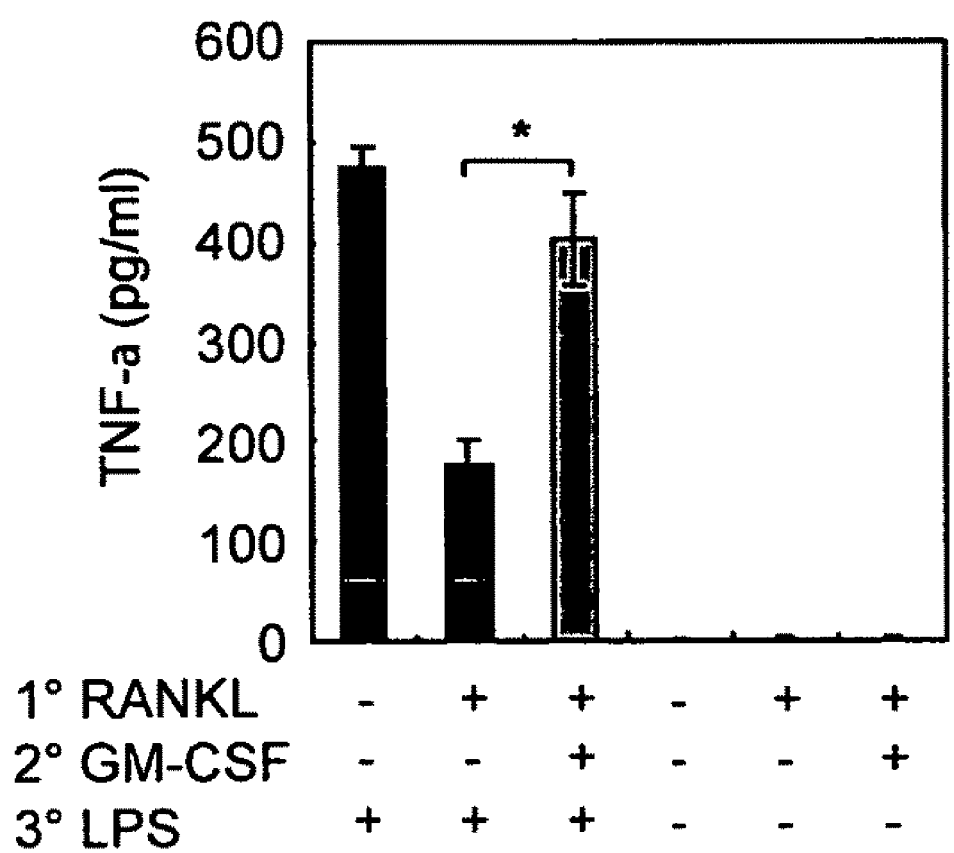
FIG. 8 shows attenuation of RANKL-induced tolerance by GM-CSF.

GM-CSF is known to inhibit RANKL/RANK signaling. Hence, the effects of GM-CSF on RANKL-induced tolerance were examined. MDSMs were pretreated with soluble RANKL for 24 hours and then treated with soluble RANKL-free GM-CSF-containing medium for 3 hours. Subsequently, cells were stimulated with LPS and then TNF-α concentrations were measured. Specifically, MDBMs were treated with 10 ng/ml soluble RANKL for 24 hours (1°), stimulated with 500 U/ml GM-CSF for 3 hours (2°), and then stimulated with 100 ng/ml LPS for 6 hours (3°). The results are shown in FIG. 8. TNF-α concentrations (n=3) in the culture supernatants were measured by ELISA. Bars in FIG. 8 represent means±SD. *, P<0.01. Data representative among three experiments are shown. As shown in FIG. 8, although GM-CSF itself did not induce TNF-α production, brief treatment with GM-CSF significantly increased TNF-α production in macrophages pretreated with soluble RANKL. These results suggest that GM-CSF attenuates RANKL-induced tolerance (FIG. 8). Taken together, it was demonstrated by the Example that short treatment with GM-CSF can restore the responsiveness of macrophages to LPS, as in the case of soluble RANKL removal.

(3) Dynamic Shift of Serum Soluble RANKL and OPG Levels Due to LPS Administration and Bacterial Infection To compare physiological and pathological soluble RANKL concentrations in serum, LPS was injected intraperitoneally into mice and then serum soluble RANKL and OPG concentrations were measured. LPS was injected intraperitoneally into C57BL/6J mice (n=24) (1 μg/g body weight). Blood was collected at each time point as in FIG. 9 (n=3, mouse/point). Serum soluble RANKL and OPG concentrations were measured by ELISA. The serum soluble RANKL concentration was approximately 150 pg/ml and OPG concentration was approximately 2000 pg/ml prior to LPS injection. The results are shown in FIGS. 9A and B. Bars in FIG. 9 represent means±SD. "*, P<0.05; **, P<0.01" show the results compared with that of 0 h. Surprisingly, soluble RANKL concentration dramatically fell at 6 hours after LPS injection, while OPG concentration was up-regulated on hour 6 and later. Furthermore, C57BL/6J mice (n=6) were orally infected with $3.3 \times 10^7$ CFU/g body weight of *Salmonella* (infection). Control mice were caused to drink PBS (control). After 4 days, blood was collected and then serum soluble RANKL and OPG concentrations were measured by ELISA. The results are shown in FIGS. 10A and B. As shown in FIG. 10, down-regulation of serum soluble RANKL and up-regulation of OPG were also observed on day 4 after oral infection with *Salmonella*. Bars in FIG. 10 represent means±SD (n=3). *, P<0.05; **, P<0.01. These results demonstrate that serum soluble RANKL and OPG levels are dynamically regulated in response to LPS and bacterial infection.

(4) Abnormal Cytokine Production in Mice Lacking RANKL and Mice Lacking OPG

To examine the effects of physiological serum soluble RANKL on LPS-induced cytokine production, $Tnfsf11^{-/-}$ mice lacking RANKL were analyzed. FIGS. 11A and B show serum soluble RANKL and OPG concentrations in wild-type mice and mice lacking RANKL ($Tnfsf11^{-/-}$), as measured by ELISA (n=4 for each genotype). Bars in FIG. 11 represent means±SD. "*, P<0.05; **, P<0.01" show the results compared with that of the control. As predicted, serum soluble RANKL was not detectable in $Tnfsf11^{-/-}$ mice, but OPG levels were slightly higher in $Tnfsf11^{-/-}$ mice than in wild-type mice.

Figure 12:
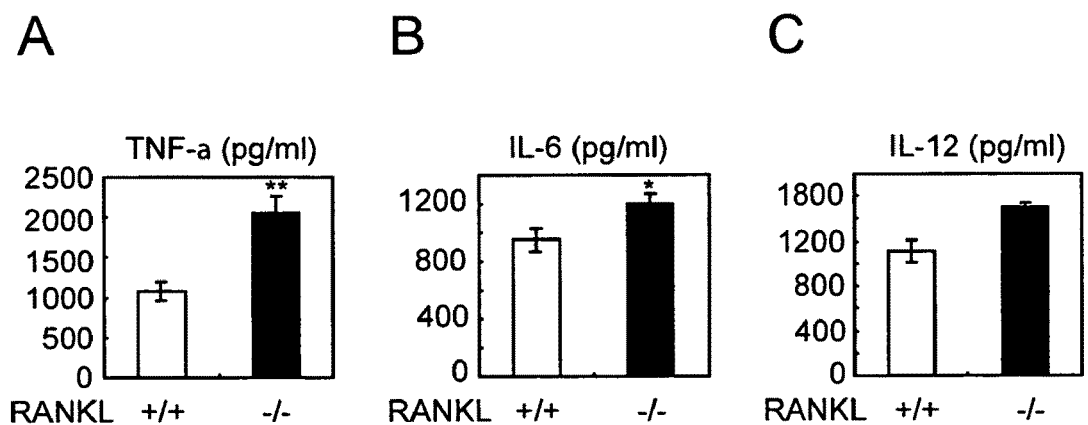
FIG. 12 shows serum cytokine concentrations in wild-type mice and mice lacking RANKL (Tnfsf11$^{-/-}$) into which LPS was injected intraperitoneally.

Furthermore, LPS (2 μg/g body weight) was injected intraperitoneally. Ninety minutes later, blood of wild-type mice and $Tnfrsf11^{-/-}$ mice were collected. Serum cytokines were measured by ELISA. After LPS injection, significantly elevated TNF-α production and IL-6 production were observed in $Tnfsf11^{-/-}$ mice (FIG. 12A to C). Bars in FIG. 12 represent means±SD. "*, P<0.05; **, P<0.01" show the results compared with that of the control. These results are consistent with the notion that the lack of RANKL-induced tolerance potentiates production of inflammatory cytokines in $Tnfsf11^{-/-}$ mice.

To further examine the role of RANKL-induced tolerance in mice, $Tnfrsf11b^{-/-}$ mice lacking OPG were analyzed. FIGS. 13A and B show serum soluble RANKL and OPG concentrations in wild-type mice and mice lacking OPG ($Tnfrsf11b^{-/-}$), as measured by ELISA (n=5 for each genotype). Bars in FIG. 13 represent means±SD. "*, P<0.05; **, P<0.01" show the results compared with that of the control. Compared with control heterozygous mice lacking OPG, physiological serum soluble RANKL concentration was approximately 10 times higher in $Tnfrsf11b^{-/-}$ mice. Therefore, it can be said that mice lacking OPG are always exposed to high soluble RANKL concentrations.

Figure 14:
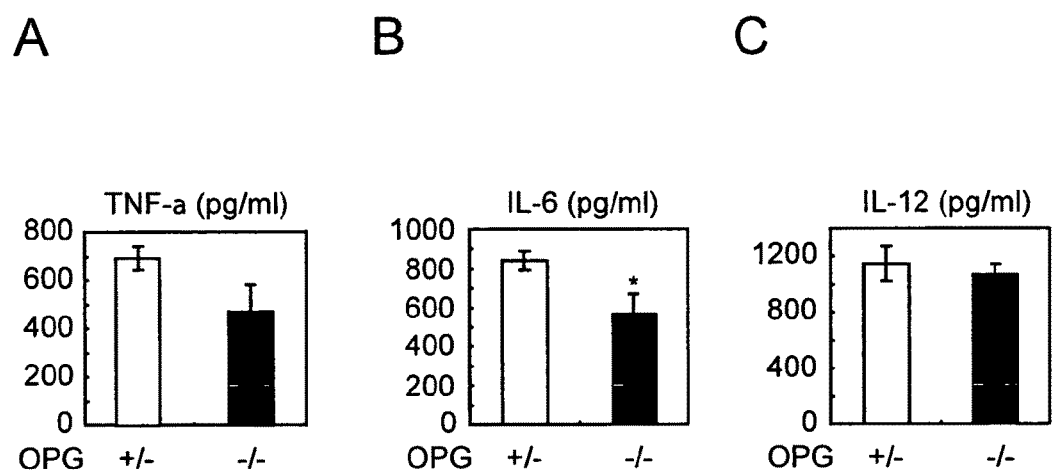
FIG. 14 shows serum cytokine concentrations in wild-type mice and mice lacking OPG (Tnfrsf11b$^{-/-}$), into which LPS was injected intraperitoneally.

Furthermore, LPS (2 μg/g body weight) was injected intraperitoneally. Ninety (90) minutes later, blood was collected from wild-type mice and $Tnfrsf11b^{-/-}$ mice and then serum cytokines were measured by ELISA. The results are shown in FIG. 14A to C. Bars in FIG. 14 represent means±SD. "*, P<0.05; **, P<0.01" show the results compared with that of the control. It was revealed that after LPS injection, IL-6 production significantly decreased in $Tnfrsf11b^{-/-}$ mice. Therefore, it was demonstrated that chronic exposure to high soluble RANKL concentrations suppresses inflammatory cytokine production in mice lacking OPG.

(5) Hypersensitivity of Mice Lacking RANKL to LPS

Figure 15:
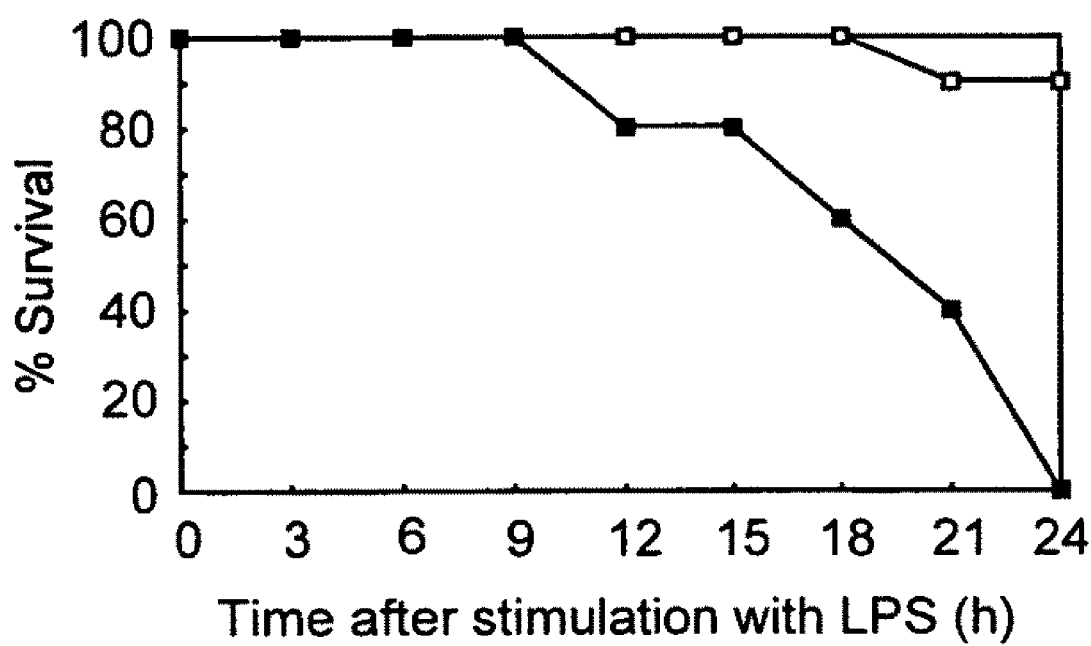
FIG. 15 shows survival curves after intraperitoneal injection of a high dose of LPS into wild-type mice (n=10) and Tnfsf11$^{-/-}$ mice (n=5).

To analyze the effects of abnormal inflammatory cytokine production in mice lacking RANKL, we intraperitoneally injected a high concentration of LPS into wild-type mice and $Tnfsf11^{-/-}$ mice and then compared the resulting survival percentages. A high dose of LPS (130 μg/g body weight) was intraperitoneally injected into 6-week-old wild-type mice (n=10) and $Tnfsf11^{-/-}$ mice (n=5), and then survival curves were generated. As a result, while 90% of wild-type mice (n=10, open square) survived at 24 hours after injection, all $Tnfsf11^{-/-}$ mice (n=5, close square) died within 24 hours (FIG. 15). $Tnfsf11^{-/-}$ mice were hypersensitive to LPS. These results suggest that physiological serum soluble RANKL functions to protect mice from endotoxin shock.

(6) Decreased TLR4 by Soluble RANKL

Figure 16:
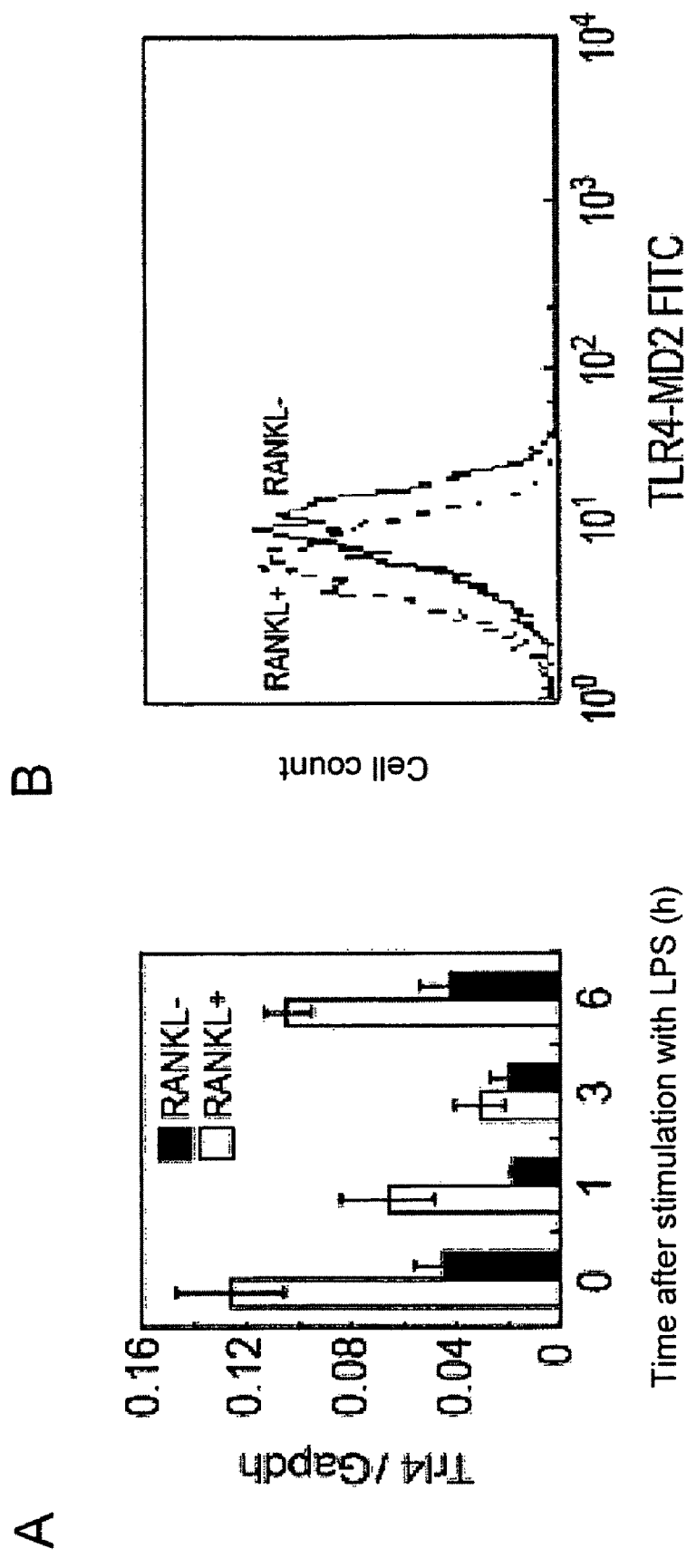
FIG. 16 shows that TLR4 expression is suppressed by treatment of macrophages with soluble RANKL.

When macrophages were treated with soluble RANKL for 24 hours, the mRNA level of TLR4 was significantly suppressed. Even when macrophages were treated with soluble RANKL, stimulated with LPS, and then the mRNA level of TLR4 at this time was observed with time, the same tendency was observed (FIG. 16A). Bars in FIG. 16 represent means±SD. Moreover, it was revealed by flow cytometry analysis that 24 hours of treatment of macrophages with soluble RANKL suppresses the expression of TLR4-MD2 complex on cell surfaces (FIG. 16B). Since TLR4 is an LPS receptor, it was suggested that such a decreased TLR4 level plays a role in the mechanism of RANKL tolerance.

(7) Suppression of Antigen Presentation by Soluble RANKL

Figure 17:
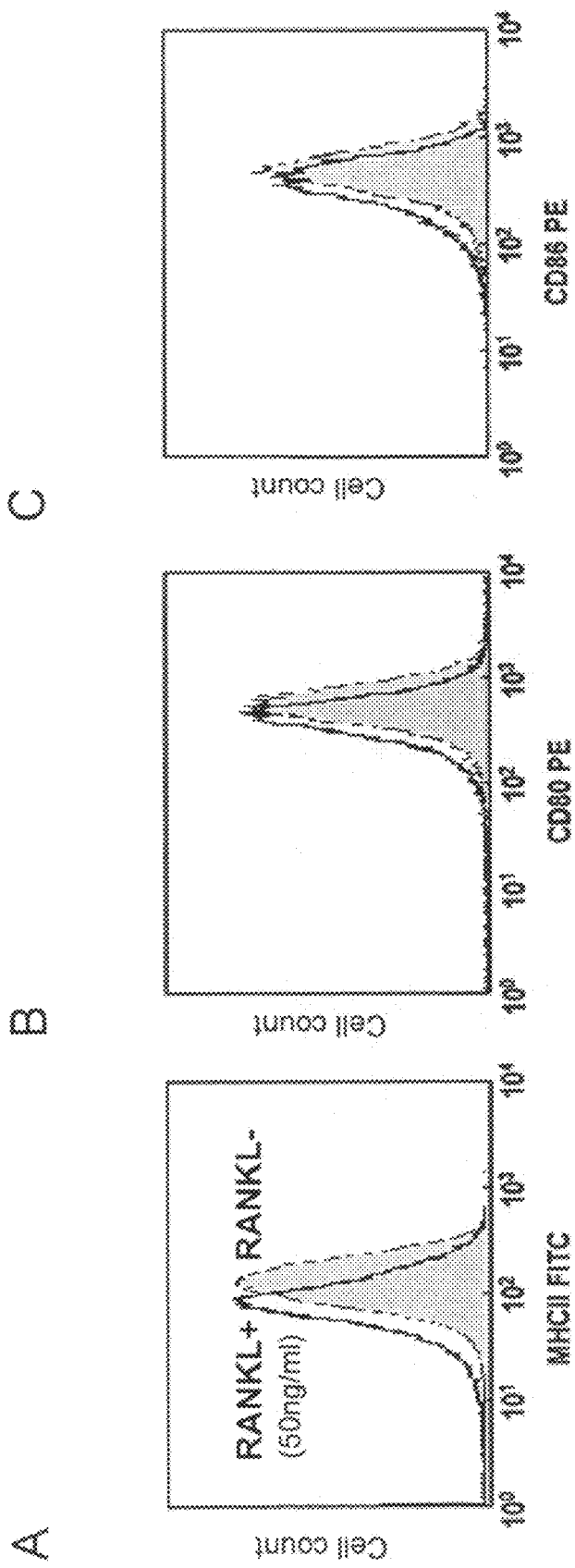
FIG. 17 shows antigen presentation suppressed by soluble RANKL.

It was revealed by flow cytometry analysis that 24 hours of treatment of macrophages with soluble RANKL results in significant decreases in the expression of MHCII, CD80, and CD86 on the surfaces (FIG. 17, continuous lines represent the results of the group treated with soluble RANKL and broken lines (gray) represent the results of the control group). MHCII is a molecule for presenting foreign antigens to lymphocytes and co-stimulatory molecules such as CD80 and CD86 are considered to be essential at this time.

Therefore, decreased expression levels of these molecules suggest that soluble RANKL is capable of suppressing antigen presentation by macrophages.

(8) c-Fos-independent RANKL Tolerance

Figure 18:
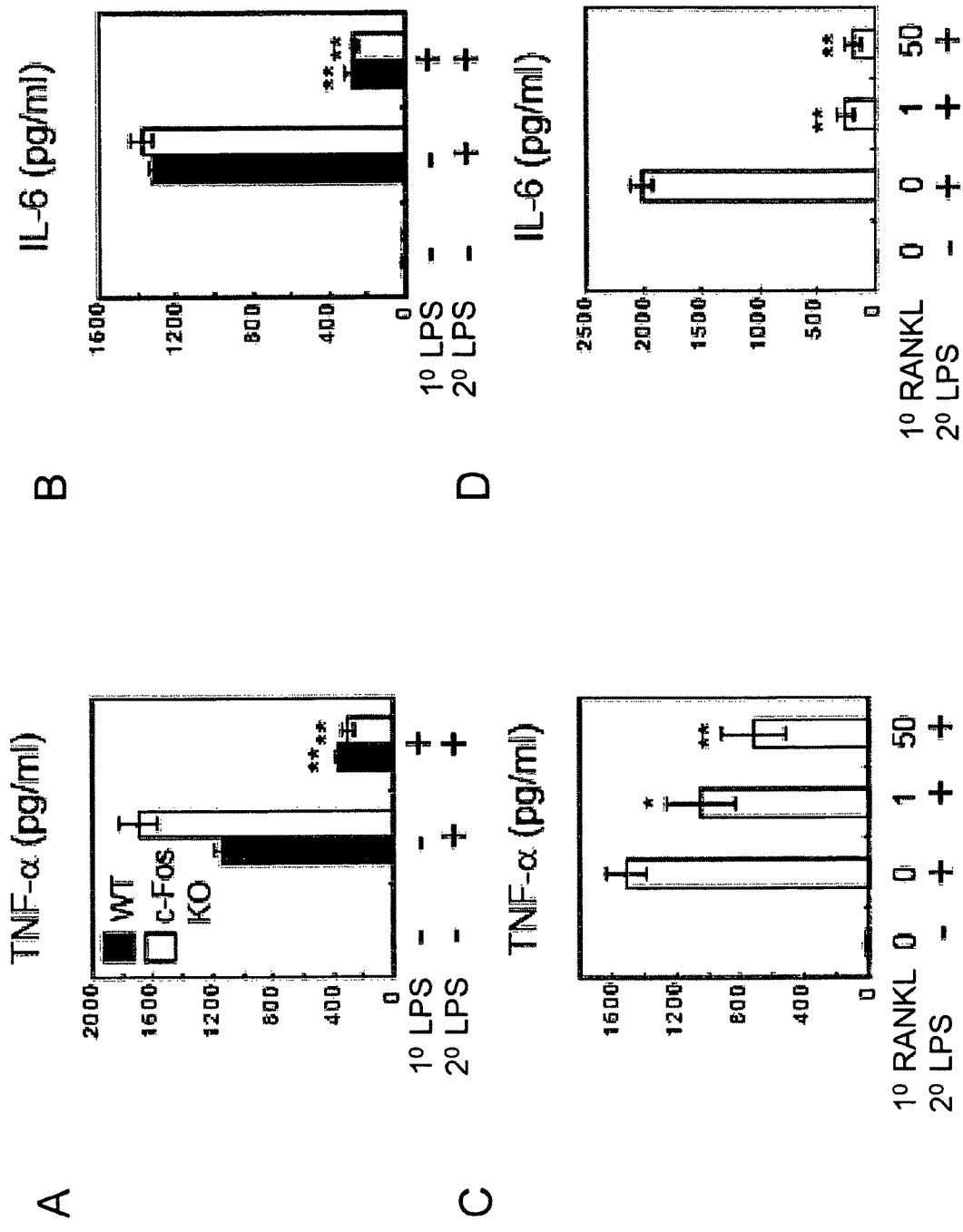
FIG. 18 shows that RANKL tolerance is c-Fos-independent.

Transduction of RANKL/RANK signal in osteoclast differentiation requires the c-Fos transcription factor. Mice lacking c-Fos are unable to produce osteoclasts. To examine whether or not c-Fos is required for RANKL tolerance to occur, macrophages derived from mice lacking c-Fos were analyzed. Macrophages derived from mice lacking c-Fos were pretreated with 1 ng/ml LPS for 24 hours and then stimulated with 100 ng/ml LPS to observe LPS tolerance. It was revealed that LPS tolerance occurred similarly to the case of the wild-type mice (FIGS. 18 A and B). Moreover, macrophages derived from the same were pretreated with 10 ng/ml soluble RANKL for 24 hours and then stimulated with 100 ng/ml LPS to observe RANKL tolerance. Thus, it was also revealed that RANKL tolerance occurred similarly to the case of the wild-type mice (FIGS. 18 C and D). Bars in FIG. 18 represent means±SD. Therefore, it can be concluded that LPS tolerance or RANKL tolerance is c-Fos-independent.

That is, RANKL tolerance should not be considered to be only the "phenomenon of macrophage differentiation" in the process during which macrophages differentiate into multinucleated osteoclasts.

(9) Mouse Acute Toxicity Test

Mice used herein were 7- to 8-week-old C57BL/6N (female) mice.

LPS used herein was Lipopolysaccharides from *Escherichia coli* O55:B5 (Sigma). Sterile water (1.0 ml) was added to 10 mg each of LPS for dissolution and then the solution was used. M-CSF used herein was Leukoprol (KYOWA HAKKO KOGYO Co., Ltd.). PBS (1.0 ml) was added to 50 µg each of M-CSF for dissolution and then the solution was used.

Preparation of GST-RANKL

Figure 20:
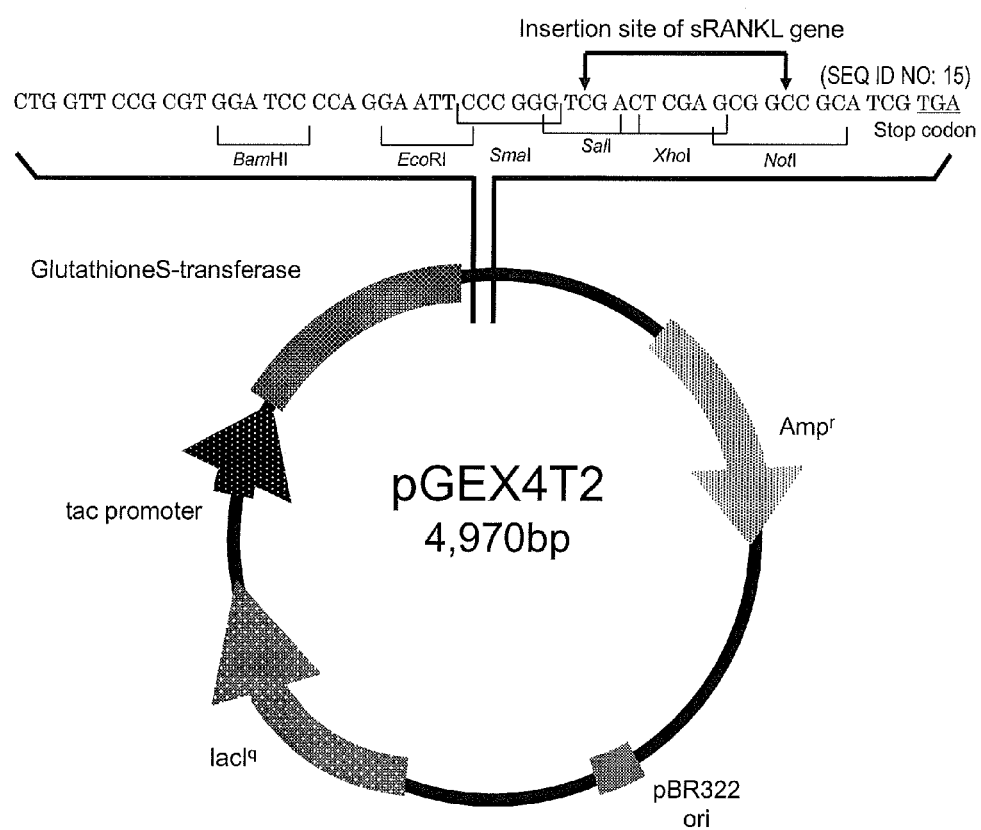
FIG. 20 shows a restriction enzyme map of a vector containing a RANKL gene (SEQ ID No: 15).

Sal I, Not I site was added to cDNA encoding human-type RANKL residues 140 to 317 by PCR. With the use of these endonucleases, the sequence was cloned downstream of Glutathione S-transferase of pGEX-4T-2 (GE healthcare; Genbank Accession Number U13854). The nucleotide sequence of cDNA encoding human-type RANKL residues 140 to 317 (SEQ ID No: 14) and the corresponding amino acid sequence (SEQ ID No: 10) are shown in FIG. 19. Moreover, the restriction enzyme map of a vector containing the RANKL gene (SEQ ID No: 15) is shown in FIG. 20. Furthermore, the nucleotide sequence of the vector (SEQ ID No: 11) is shown in FIGS. 21A and 21B. The nucleotide sequence in FIG. 21B is continued from the nucleotide sequence in FIG. 21A. After induction of IPTG (final concentration: 0.5 mM)-mediated protein expression in BL21 (DE3) *Escherichia coli* (Invitrogen), microbes were suspended in an extraction buffer (50 mM Tris-HCl, pH 8.0, 100 mM NaCl, 1 mM EDTA, 1 mM DTT, and 1% (v/v) TritonX-100) and then disrupted at 4° C. using an ultrasonicator. After centrifugation at 18000×g for 15 minutes, the supernatants were collected and then subjected to a Glutathione Sepharose (Trademark) column. Subsequently, the resultants were washed with a buffer for washing (50 mM Tris-HCl, pH 8.0, 100 mM NaCl, 1 mM DTT, and 0.1% (v/v) TritonX-100). Subsequently, elution was performed with a Glutathione solution (20 mM reduced glutathione, 50 mM Tris-HCl, and pH 8.0). The molecular weight and the purity of GST-RANKL purified by SDS-PAGE were confirmed, followed by filtration. The molecular weight was 47.0 kDa and the purity was 95% or higher. Furthermore, endotoxin concentrations were measured by limulus amebocyte lysate assay, so that the concentrations were confirmed to be less than 1 EU/µg.

Figure 22:
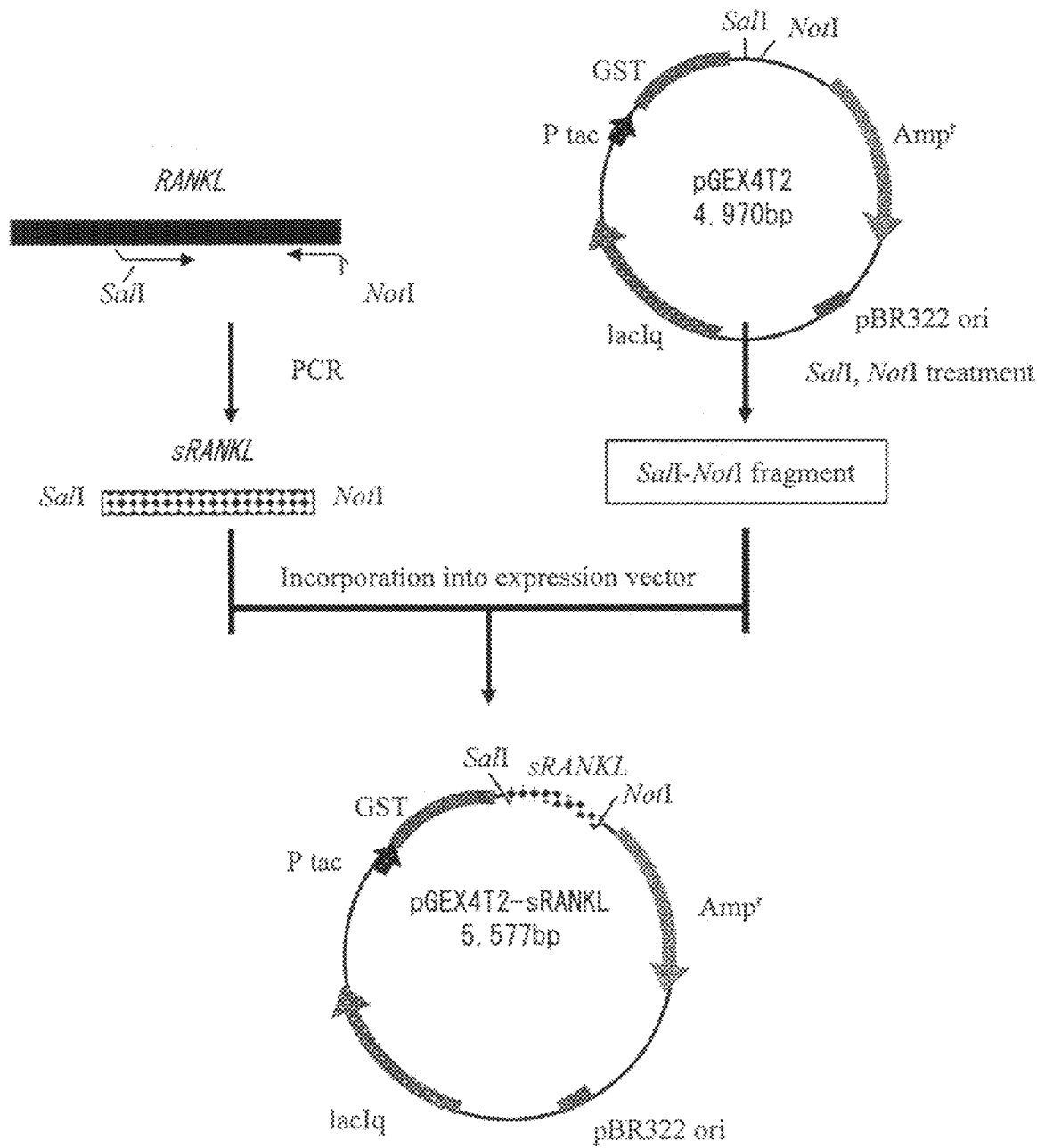
FIG. 22 shows a method for construction of a GST-RANKL vector.

A method for constructing a GST-RANKL expression vector is shown in FIG. 22.

Test of Administration of LPS, RANKL, and M-CSF

Ten (10) µg of GST-RANKL, 2 µg of M-CSF, 2 µg of M-CSF+10 µg of GST-RANKL, and PBS as a control were separately administered intraperitoneally to C57BL/6N mice (9 to 10 mice per group). After 24 hours, LPS (2.5 mg/mouse) was administered intraperitoneally. Subsequent survival was observed until hour 144 after the administration.

The results are shown in FIG. 23. As shown in FIG. 23, survival % was significantly high (P<0.03) when RANKL and M-CSF had been administered.

All publications, patents, and patent applications cited herein are incorporated herein by reference in their entirety.

Sequence Listing Free Text

SEQ ID NOS: 3 and 4: GST-RANKL (aa127-317)
SEQ ID NOS: 5 and 6: GST-RANKL (aa140-317)
SEQ ID NOS: 7 and 8: GST-RANKL (aa159-317)
SEQ ID NOS: 9 to 13: synthesis

The invention claimed is:

1. A method for detection of a bacterial infectious disease or sepsis with use of RANKL as a marker in a biological blood sample, the method comprising:
  (i) measuring by immunoassay a concentration of soluble RANKL in the biological blood sample isolated from a subject; and
  (ii) determining that the subject is affected with the bacterial infectious disease or sepsis when the concentration of the soluble RANKL in the biological blood sample is lower than that of a normal subject,
  wherein the bacterial infectious disease is a salmonella infectious disease, and
  the sepsis is lipopolysaccharide or (LPS)-induced sepsis.

2. The method for detection of a bacterial infectious disease or sepsis according to claim 1, wherein the method uses OPG in addition to RANKL as a marker in the biological blood sample, and the method comprises:
  (i) measuring by immunoassay a concentration of OPG in the biological blood sample isolated from the subject in addition to the concentration of soluble RANKL; and
  (ii) determining that the subject is affected with bacterial infectious disease or sepsis when a ratio of the concentration of the soluble RANKL relative to the concentration of the OPG in the biological blood sample is lower than the ratio of a normal subject.

3. The method for detection of a bacterial infectious disease or sepsis according to claim 2, the method comprising a step of isolating the blood sample from the subject.

4. The method for detection of a bacterial infectious disease or sepsis according to claim 1, the method comprising a step of isolating the blood sample from the subject.

* * * * *